(12) United States Patent
Barry

(10) Patent No.: US 7,473,252 B2
(45) Date of Patent: Jan. 6, 2009

(54) SYSTEMS AND METHODS FOR SHRINKING AND/OR SECURING CARDIOVASCULAR TISSUE

(75) Inventor: Robert L. Barry, Kirkland, WA (US)

(73) Assignee: Coaptus Medical Corporation, Redmond, WA (US)

( * ) Notice: Subject to any disclaimer, the term of this patent is extended or adjusted under 35 U.S.C. 154(b) by 595 days.

(21) Appl. No.: 11/243,324

(22) Filed: Oct. 4, 2005

(65) Prior Publication Data

US 2006/0079870 A1    Apr. 13, 2006

Related U.S. Application Data

(60) Provisional application No. 60/617,247, filed on Oct. 7, 2004.

(51) Int. Cl.
   *A61B 18/18* (2006.01)
   *A61N 1/05* (2006.01)
(52) U.S. Cl. .................. 606/41; 606/49; 607/122
(58) Field of Classification Search ............ 606/32, 606/49; 607/96, 122
   See application file for complete search history.

(56) References Cited

U.S. PATENT DOCUMENTS

| | | |
|---|---|---|
| 2,582,628 A | 1/1952 | Halloran |
| 3,862,627 A | 1/1975 | Hans, Sr. |
| 4,273,127 A | 6/1981 | Auth et al. |
| 4,492,231 A | 1/1985 | Auth |
| 4,532,924 A | 8/1985 | Auth et al. |
| 4,556,065 A | 12/1985 | Hoffmann |
| 4,799,479 A | 1/1989 | Spears |
| 4,813,926 A | 3/1989 | Kerwin |
| 4,822,348 A | 4/1989 | Casey |
| 4,832,048 A | 5/1989 | Cohen |
| 4,850,960 A | 7/1989 | Grayzel |
| 4,892,098 A | 1/1990 | Sauer |

(Continued)

FOREIGN PATENT DOCUMENTS

WO    WO-87/04081 A1    7/1987

(Continued)

OTHER PUBLICATIONS

U.S. Appl. No. 60/458,854, Gifford.

(Continued)

*Primary Examiner*—Fenn C Mathew
*Assistant Examiner*—Kaitlyn E Helling
(74) *Attorney, Agent, or Firm*—Perkins Coie LLP

(57) ABSTRACT

Systems and methods for treating cardiac tissue are disclosed. A method in accordance with one embodiment of the invention is directed to treating cardiac tissue that includes a primum, a secundum adjacent to the primum, and a patent foramen ovale (PFO). The method can include shrinking the primum at a first location spaced apart from the PFO, and at least partially sealing the PFO by applying energy at a second location at least closer to the PFO than the first location. A variety of techniques, including vacuum, mechanical, chemical, RF energy and ultrasound can be used to shrink the primum. In at least some embodiments, shrinking the primum can be performed independently of whether a PFO is also sealed, for example, if the patient receiving the treatment does not have a PFO.

42 Claims, 9 Drawing Sheets

U.S. PATENT DOCUMENTS

| | | | |
|---|---|---|---|
| 4,929,246 A | 5/1990 | Sinofsky | |
| 5,056,517 A | 10/1991 | Fenici | |
| 5,071,417 A | 12/1991 | Sinofsky | |
| 5,122,137 A | 6/1992 | Lennox | |
| 5,156,613 A | 10/1992 | Sawyer | |
| 5,207,670 A | 5/1993 | Sinofsky | |
| 5,290,272 A | 3/1994 | Burstein et al. | |
| 5,290,278 A | 3/1994 | Anderson | |
| 5,298,224 A | 3/1994 | Plum | |
| 5,300,065 A | 4/1994 | Anderson | |
| 5,334,191 A | 8/1994 | Poppas et al. | |
| 5,336,221 A | 8/1994 | Anderson | |
| 5,364,389 A | 11/1994 | Anderson | |
| 5,405,322 A | 4/1995 | Lennox et al. | |
| 5,409,479 A | 4/1995 | Dew et al. | |
| 5,409,481 A | 4/1995 | Poppas et al. | |
| 5,421,338 A | 6/1995 | Crowley et al. | |
| 5,451,235 A | 9/1995 | Lock et al. | |
| 5,454,807 A | 10/1995 | Lennox et al. | |
| 5,505,730 A | 4/1996 | Edwards | |
| 5,507,744 A | 4/1996 | Tay et al. | |
| 5,522,873 A | 6/1996 | Jackman et al. | |
| 5,540,677 A | 7/1996 | Sinofsky | |
| 5,545,195 A | 8/1996 | Lennox et al. | |
| 5,569,239 A | 10/1996 | Sinofsky | |
| 5,571,088 A | 11/1996 | Lennox et al. | |
| 5,571,216 A | 11/1996 | Anderson | |
| 5,575,722 A * | 11/1996 | Saia et al. | 473/300 |
| 5,575,772 A | 11/1996 | Lennox | |
| 5,584,872 A | 12/1996 | LaFontaine et al. | |
| 5,611,794 A | 3/1997 | Sauer et al. | |
| 5,643,171 A | 7/1997 | Bradshaw et al. | |
| 5,658,280 A | 8/1997 | Issa | |
| 5,662,643 A | 9/1997 | Kung et al. | |
| 5,662,647 A | 9/1997 | Crow et al. | |
| 5,669,934 A | 9/1997 | Sawyer | |
| 5,695,493 A | 12/1997 | Nakajima et al. | |
| 5,702,421 A | 12/1997 | Schneidt | |
| 5,709,224 A | 1/1998 | Behl et al. | |
| 5,713,891 A | 2/1998 | Poppas | |
| 5,725,512 A | 3/1998 | Swartz et al. | |
| 5,725,522 A | 3/1998 | Sinofsky | |
| 5,725,552 A | 3/1998 | Kotula et al. | |
| 5,749,895 A | 5/1998 | Sawyer et al. | |
| 5,757,772 A | 5/1998 | Thornberg et al. | |
| 5,782,848 A | 7/1998 | Lennox | |
| 5,782,860 A | 7/1998 | Epstein et al. | |
| 5,810,810 A | 9/1998 | Tay et al. | |
| 5,824,015 A | 10/1998 | Sawyer | |
| 5,827,265 A | 10/1998 | Glinsky et al. | |
| 5,827,268 A | 10/1998 | Laufer | |
| 5,865,827 A | 2/1999 | Bullister | |
| 5,868,702 A | 2/1999 | Stevens et al. | |
| 5,873,828 A | 2/1999 | Fujio et al. | |
| 5,897,551 A | 4/1999 | Everett et al. | |
| 5,919,188 A | 7/1999 | Shearon et al. | |
| 5,919,191 A | 7/1999 | Lennox et al. | |
| 5,919,200 A | 7/1999 | Stambaugh et al. | |
| 5,925,078 A | 7/1999 | Anderson | |
| 5,928,224 A | 7/1999 | Laufer | |
| 5,928,266 A | 7/1999 | Kontos | |
| 5,931,165 A | 8/1999 | Reich et al. | |
| 5,944,738 A | 8/1999 | Amplatz et al. | |
| 5,957,919 A | 9/1999 | Laufer | |
| 5,964,782 A | 10/1999 | Lafontaine et al. | |
| 5,972,026 A | 10/1999 | Laufer et al. | |
| 5,984,909 A | 11/1999 | Lurie et al. | |
| 5,989,284 A | 11/1999 | Laufer | |
| 6,004,269 A | 12/1999 | Crowley et al. | |
| 6,004,316 A | 12/1999 | Laufer | |
| 6,010,516 A | 1/2000 | Hulka | |
| 6,033,397 A | 3/2000 | Laufer et al. | |
| 6,033,398 A | 3/2000 | Farley et al. | |
| 6,036,687 A | 3/2000 | Laufer et al. | |
| 6,048,333 A | 4/2000 | Lennox et al. | |
| 6,063,081 A | 5/2000 | Mulier et al. | |
| 6,063,085 A | 5/2000 | Tay et al. | |
| 6,066,126 A | 5/2000 | Li et al. | |
| 6,068,653 A | 5/2000 | LaFontaine | |
| 6,071,277 A | 6/2000 | Farley et al. | |
| 6,071,303 A | 6/2000 | Laufer | |
| 6,083,219 A | 7/2000 | Laufer | |
| 6,083,223 A | 7/2000 | Baker | |
| 6,083,255 A | 7/2000 | Laufer et al. | |
| 6,086,586 A | 7/2000 | Hooven | |
| 6,087,552 A | 7/2000 | Gregory | |
| 6,091,995 A | 7/2000 | Ingle et al. | |
| 6,106,520 A | 8/2000 | Laufer et al. | |
| 6,128,522 A | 10/2000 | Acker et al. | |
| 6,132,429 A | 10/2000 | Baker | |
| 6,135,997 A | 10/2000 | Laufer et al. | |
| 6,139,527 A | 10/2000 | Laufer et al. | |
| 6,149,660 A | 11/2000 | Laufer et al. | |
| 6,152,139 A | 11/2000 | Laufer | |
| 6,156,032 A | 12/2000 | Lennox | |
| 6,165,206 A | 12/2000 | Tu | |
| 6,168,594 B1 | 1/2001 | LaFontaine et al. | |
| 6,200,315 B1 | 3/2001 | Gaiser et al. | |
| 6,200,333 B1 | 3/2001 | Laufer | |
| 6,206,907 B1 | 3/2001 | Marino et al. | |
| 6,210,411 B1 | 4/2001 | Hofmann et al. | |
| 6,211,335 B1 | 4/2001 | Owen et al. | |
| 6,212,426 B1 | 4/2001 | Swanson | |
| 6,221,068 B1 | 4/2001 | Fried et al. | |
| 6,238,389 B1 | 5/2001 | Paddock et al. | |
| 6,254,598 B1 | 7/2001 | Edwards et al. | |
| 6,254,601 B1 | 7/2001 | Burbank et al. | |
| 6,257,241 B1 | 7/2001 | Wampler | |
| 6,258,087 B1 | 7/2001 | Edwards et al. | |
| 6,273,886 B1 | 8/2001 | Edwards et al. | |
| 6,273,907 B1 | 8/2001 | Laufer | |
| 6,283,935 B1 | 9/2001 | Laufer et al. | |
| 6,283,962 B1 | 9/2001 | Tu et al. | |
| 6,283,988 B1 | 9/2001 | Laufer et al. | |
| 6,283,989 B1 | 9/2001 | Laufer et al. | |
| 6,290,674 B1 | 9/2001 | Roue et al. | |
| 6,299,633 B1 | 10/2001 | Laufer | |
| 6,302,898 B1 | 10/2001 | Edwards et al. | |
| 6,323,037 B1 | 11/2001 | Lauto et al. | |
| 6,325,798 B1 | 12/2001 | Edwards et al. | |
| 6,338,731 B1 | 1/2002 | Laufer et al. | |
| 6,352,534 B1 | 3/2002 | Paddock et al. | |
| 6,355,030 B1 | 3/2002 | Aldrich et al. | |
| 6,355,031 B1 | 3/2002 | Edwards et al. | |
| 6,358,245 B1 | 3/2002 | Edwards et al. | |
| 6,375,615 B1 | 4/2002 | Flaherty et al. | |
| 6,379,368 B1 | 4/2002 | Corcoran et al. | |
| 6,383,198 B1 | 5/2002 | Hamilton | |
| 6,391,048 B1 | 5/2002 | Ginn et al. | |
| 6,391,049 B1 | 5/2002 | McNally et al. | |
| 6,398,779 B1 | 6/2002 | Buysse et al. | |
| 6,398,782 B1 | 6/2002 | Pecor et al. | |
| 6,398,797 B2 | 6/2002 | Bombard et al. | |
| 6,401,719 B1 | 6/2002 | Farley et al. | |
| 6,401,720 B1 | 6/2002 | Stevens et al. | |
| 6,419,669 B1 | 7/2002 | Frazier et al. | |
| 6,438,424 B1 | 8/2002 | Knowlton | |
| 6,440,128 B1 | 8/2002 | Edwards et al. | |
| 6,440,152 B1 | 8/2002 | Gainor et al. | |
| 6,453,202 B1 | 9/2002 | Knowlton | |
| 6,461,314 B1 | 10/2002 | Pant et al. | |
| 6,463,332 B1 | 10/2002 | Aldrich | |
| 6,464,626 B1 | 10/2002 | Peterson | |
| 6,464,689 B1 | 10/2002 | Qin et al. | |

| | | | | | |
|---|---|---|---|---|---|
| 6,470,216 B1 | 10/2002 | Knowlton | 2002/0151871 A1 | 10/2002 | Gaiser et al. |
| 6,482,203 B2 | 11/2002 | Paddock et al. | 2002/0169377 A1 | 11/2002 | Khairkhahan et al. |
| 6,488,673 B1 | 12/2002 | Laufer et al. | 2002/0183787 A1 | 12/2002 | Wahr et al. |
| 6,494,879 B2 | 12/2002 | Lennox et al. | 2002/0183789 A1 | 12/2002 | Neev |
| 6,494,888 B1 | 12/2002 | Laufer et al. | 2002/0193787 A1 | 12/2002 | Qin et al. |
| 6,506,196 B1 | 1/2003 | Laufer | 2002/0193816 A1 | 12/2002 | Laufer et al. |
| 6,520,185 B1 | 2/2003 | Bommannan et al. | 2003/0009194 A1 | 1/2003 | Saker et al. |
| 6,524,326 B1 | 2/2003 | Zhu et al. | 2003/0024538 A1 | 2/2003 | Edwards et al. |
| 6,526,302 B2 | 2/2003 | Hassett | 2003/0028188 A1 | 2/2003 | Paddock et al. |
| 6,529,778 B2 | 3/2003 | Prutchi | 2003/0028189 A1 | 2/2003 | Woloszko et al. |
| 6,547,776 B1 | 4/2003 | Gaiser et al. | 2003/0050632 A1 | 3/2003 | Fjield et al. |
| 6,554,827 B2 | 4/2003 | Chandrasekaran et al. | 2003/0069570 A1 | 4/2003 | Witzel et al. |
| 6,558,366 B1 | 5/2003 | Drasler et al. | 2003/0078578 A1 | 4/2003 | Truckai et al. |
| 6,562,034 B2 | 5/2003 | Edwards et al. | 2003/0092689 A1 | 5/2003 | Escandon et al. |
| 6,562,037 B2 | 5/2003 | Paton et al. | 2003/0093071 A1 | 5/2003 | Hauck et al. |
| 6,562,052 B2 | 5/2003 | Nobles et al. | 2003/0130730 A1 | 7/2003 | Cohn et al. |
| 6,565,557 B1 | 5/2003 | Sporri et al. | 2003/0135206 A1 | 7/2003 | Edwards et al. |
| 6,575,971 B2 | 6/2003 | Hauck et al. | 2003/0144652 A1 | 7/2003 | Baket et al. |
| 6,577,902 B1 | 6/2003 | Laufer et al. | 2003/0144694 A1 | 7/2003 | Chanduszko et al. |
| 6,583,117 B2 | 6/2003 | Owen et al. | 2003/0158551 A1 | 8/2003 | Paton et al. |
| 6,589,238 B2 | 7/2003 | Edwards et al. | 2003/0178032 A1 | 9/2003 | Ingle et al. |
| 6,595,934 B1 | 7/2003 | Hissong et al. | 2003/0191511 A1 | 10/2003 | Laufer et al. |
| 6,602,251 B2 | 8/2003 | Burbank et al. | 2003/0191512 A1 | 10/2003 | Laufer et al. |
| 6,605,084 B2 | 8/2003 | Acker et al. | 2003/0195511 A1 | 10/2003 | Barry |
| 6,606,513 B2 | 8/2003 | Lardo et al. | 2003/0195593 A1 | 10/2003 | Ingle et al. |
| 6,613,047 B2 | 9/2003 | Edwards | 2003/0195604 A1 | 10/2003 | Ingle et al. |
| 6,629,534 B1 | 10/2003 | St. Goar et al. | 2003/0208232 A1 | 11/2003 | Blaeser et al. |
| 6,629,951 B2 | 10/2003 | Laufer et al. | 2004/0003819 A1 | 1/2004 | St. Goar et al. |
| 6,635,052 B2 | 10/2003 | Loeb | 2004/0039312 A1 | 2/2004 | Hillstead et al. |
| 6,635,054 B2 | 10/2003 | Fjield et al. | 2004/0059347 A1 | 3/2004 | Hamilton |
| 6,645,198 B1 | 11/2003 | Bommannan et al. | 2004/0143294 A1 | 7/2004 | Corcoran et al. |
| 6,663,622 B1 | 12/2003 | Foley et al. | 2004/0176752 A1 | 9/2004 | Alfano et al. |
| 6,663,639 B1 | 12/2003 | Laufer et al. | 2004/0193147 A1* | 9/2004 | Malecki et al. ................ 606/32 |
| 6,669,655 B1 | 12/2003 | Acker et al. | 2004/0230185 A1 | 11/2004 | Malecki et al. |
| 6,669,687 B1 | 12/2003 | Saadat | 2004/0243122 A1* | 12/2004 | Auth et al. .................... 606/41 |
| 6,672,312 B2 | 1/2004 | Acker | 2004/0267191 A1 | 12/2004 | Gifford et al. |
| 6,673,070 B2 | 1/2004 | Edwards et al. | 2005/0021016 A1 | 1/2005 | Malecki et al. |
| 6,676,685 B2 | 1/2004 | Pedros et al. | 2005/0033288 A1 | 2/2005 | Auth et al. |
| 6,699,243 B2 | 3/2004 | West et al. | 2005/0034735 A1 | 2/2005 | Deem et al. |
| 6,702,835 B2 | 3/2004 | Ginn | 2005/0055050 A1 | 3/2005 | Alfaro |
| 6,706,039 B2 | 3/2004 | Mulier et al. | 2005/0065506 A1 | 3/2005 | Phan |
| 6,712,074 B2 | 3/2004 | Edwards et al. | 2005/0070923 A1 | 3/2005 | McIntosh |
| 6,712,814 B2 | 3/2004 | Edwards et al. | 2005/0080406 A1 | 4/2005 | Malecki et al. |
| 6,719,770 B2 | 4/2004 | Laufer et al. | 2005/0131401 A1 | 6/2005 | Malecki et al. |
| 6,723,092 B2 | 4/2004 | Brown et al. | 2005/0131460 A1* | 6/2005 | Gifford et al. .............. 606/215 |
| 6,728,565 B2 | 4/2004 | Wendlandt | 2005/0187568 A1 | 8/2005 | Klenk et al. |
| 6,733,495 B1 | 5/2004 | Bek et al. | 2005/0192627 A1 | 9/2005 | Whisenant et al. |
| 6,733,498 B2 | 5/2004 | Paton et al. | 2005/0192654 A1 | 9/2005 | Chanduszko et al. |
| 6,775,575 B2 | 8/2004 | Bommannan et al. | 2005/0228283 A1 | 10/2005 | Gifford et al. |
| 6,776,784 B2 | 8/2004 | Ginn | 2005/0267464 A1 | 12/2005 | Truckai et al. |
| 6,782,565 B2 | 8/2004 | Hinton | 2005/0267523 A1 | 12/2005 | Devellian et al. |
| 6,783,523 B2 | 8/2004 | Qin et al. | 2005/0267524 A1 | 12/2005 | Chanduszko |
| 6,790,207 B2 | 9/2004 | Utley et al. | 2005/0267525 A1 | 12/2005 | Chanduszko |
| 6,802,841 B2 | 10/2004 | Utley et al. | 2005/0267526 A1 | 12/2005 | Wahr et al. |
| 6,821,285 B2 | 11/2004 | Laufer et al. | 2006/0009800 A1 | 1/2006 | Christianson et al. |
| 6,827,713 B2 | 12/2004 | Bek et al. | 2006/0036282 A1 | 2/2006 | Wahr et al. |
| 6,836,688 B2 | 12/2004 | Ingle et al. | 2006/0036284 A1 | 2/2006 | Blaeser et al. |
| 6,852,108 B2 | 2/2005 | Barry et al. | 2006/0074410 A1* | 4/2006 | Malecki et al. ................ 606/32 |
| 6,866,663 B2 | 3/2005 | Edwards et al. | 2007/0060858 A1* | 3/2007 | Sogard et al. .................. 604/8 |
| 6,875,171 B2 | 4/2005 | Paolitto et al. | | | |
| 6,887,238 B2 | 5/2005 | Jahns et al. | FOREIGN PATENT DOCUMENTS | | |
| 6,939,348 B2* | 9/2005 | Malecki et al. ................ 606/41 | WO | WO-97/32532 | 9/1997 |
| 7,257,450 B2* | 8/2007 | Auth et al. .................. 607/122 | WO | WO-98/38936 | 9/1998 |
| 2001/0051800 A1 | 12/2001 | Eugeny et al. | WO | WO-99/18826 | 4/1999 |
| 2002/0042564 A1 | 4/2002 | Cooper et al. | WO | WO-99/18862 | 4/1999 |
| 2002/0068932 A1 | 6/2002 | Edwards et al. | WO | WO-99/18864 | 4/1999 |
| 2002/0082621 A1 | 6/2002 | Schurr et al. | WO | WO-99/18870 | 4/1999 |
| 2002/0091379 A1 | 7/2002 | Danek et al. | WO | WO-99/18871 | 4/1999 |
| 2002/0095164 A1 | 7/2002 | Andreas et al. | WO | WO-99/32040 | 7/1999 |
| 2002/0107512 A1 | 8/2002 | Edwards | WO | WO-99/34741 | 7/1999 |
| 2002/0107531 A1 | 8/2002 | Schreck et al. | WO | WO-99/42044 | 8/1999 |
| 2002/0128672 A1 | 9/2002 | Dinger et al. | WO | WO-99/42045 | 8/1999 |
| 2002/0143324 A1 | 10/2002 | Edwards | | | |

| | | |
|---|---|---|
| WO | WO-00/18307 | 4/2000 |
| WO | WO-00/18308 | 4/2000 |
| WO | WO-00/51510 | 9/2000 |
| WO | WO-00/57495 | 9/2000 |
| WO | WO-00/64387 | 11/2000 |
| WO | WO-00/66006 | 11/2000 |
| WO | WO-00/66015 | 11/2000 |
| WO | WO-00/66018 | 11/2000 |
| WO | WO-00/66019 | 11/2000 |
| WO | WO-00/66021 | 11/2000 |
| WO | WO-00/66052 | 11/2000 |
| WO | WO-01/10314 | 2/2001 |
| WO | WO-01/17450 | 3/2001 |
| WO | WO-02/24092 | 3/2002 |
| WO | WO-02/058780 | 8/2002 |
| WO | WO-02/060523 A2 | 8/2002 |
| WO | WO-02/060523 A3 | 8/2002 |
| WO | WO-02/067798 | 9/2002 |
| WO | WO-2004/043266 A2 | 5/2004 |
| WO | WO-2004/069055 A2 | 8/2004 |

OTHER PUBLICATIONS

U.S. Appl. No. 60/478,035, Gifford et al.
U.S. Appl. No. 60/490,082, Deem et al.
U.S. Appl. No. 11/004,634, Auth et al.
U.S. Appl. No. 60/474,055, Auth et al.
U.S. Appl. No. 60/477,760, Auth et al.
Cacecí, Dr. Thomas, Text on Skeletal Muscle and Collagen Remodeling (10 Pages).
Chapter 6: Percutaneous Closure of Heart Defects, 2002, Health Research International (3 Pages).
Chatterjee, T. et al., "Nonsurgical Closure of Secundum Atrial Septal Defect and Patent Foremen Ovale," J Clin Basic Cardiol 4:35, 2001, Bern, Switzerland (4 Pgs.).
ConMed Corporation, "Suction Instruments & Tubing," (6 Pgs.).
Gifford, H. et al., "Methods and Apparatus for Treatment of patent Foramen Ovale," http://www.freshpatents.com/Methods-and-apparatus-for-treatment-of-patent-foramen-ovale-dt20050616ptan20050131460.php, Internet pp. 1-2, Jul. 18, 2005.
Harper, R. et al., "Closure of Secundum Atrial Septal Defects With the Amplatzer Septal Occluder Device: Techniques and Problems," Catheterization and Cardiovascular Interventions, 2002, pp. 508-524, vol. 57, Wiley-Liss, Inc.
Johnston, J. H. et al., "Experimental Comparison of Endoscopic Yttrium-Aluminum-Garnet Laser, Electrosurgery, and Heater Probe for Canine Gut Arterial Coagulation: Importance of Compression and Avoidance of Erosion," Gastroenterology, 1987, pp. 1101-1108, vol. 92, No. 5, American Gastroenterological Association.
Karttunen, V. et al., "Ear Oximetry: A Noninvasive Method for Detection of Patent Foramen Ovale, A Study Comparing Dye Dilution Method and Oximetry With Contrast Transesophageal Echocardiography," Stroke, Feb. 2001, vol. 32, pp. 448-453, American Heart Association, Inc.
Kerut, E. et al., "Patent Foramen Ovale: A Review of Associated Conditions and the Impact of Physiological Size," Journal of the American College of Cardiology, Sep. 2001, pp. 613-623, vol. 38, No. 3, Elsevier Science, Inc.
Knebel, F., "Percutaneous Closure of Interatrial Communications in Adults-Prospective Embolism Prevention Study With Two and Three Dimensional Echocardiography," Cardiovascular Ultrasound, May 19, 2004, 2:5, (10 Pages).
Kramer, P., "The Hidden Connection," Endovascular Today, May 2004, pp. 47-52.
Lipton, R. et al., "Epidemiology and Economic Impact of Migraine," www.medscape.com/viewarticle/429665 <http://www.medscape.com/viewarticle/429665>, Curr Med Res Opin, 2001, 17(1s):s4-s12, Medscape.
Madison Skin & Laser Center, Thermalift™ Pre-Treatment Instructions & Thermalift™ Discharge Instructions. (2 Pages).
Malecki, W. et al., "Energy Based Devices and Methods for Treatment of Anatomic Tissue Defects," http://www.freshpatents.com/Energy-based-devices-and-methods-for-treatment-of-anatomic-tissue-defects-dt20050616ptan20050131401.php, Internet pp. 1-2, Jul. 18, 2005.
Malis, L., "Electrosurgery," J. Neurosurg., Nov. 1996, pp. 970-975, vol. 85.
Marshall, A. et al., "Structural and Compliant Anatomy of the Patent Foramen Ovale in Patients Undergoing Transcatheter Closure," American Heart Journal, Aug. 2000, pp. 303-307, vol. 140, No. 2, © Mosby, Inc.
Mayo Clinic, "Patent foremen Ovale: Paradoxical Embolism and Paradoxical Data," Mayo Clinic Proceedings, Jan. 2004, pp. 15-20, vol. 79, No. 1, Mayo Foundation for Medical Education and Research.
McClurken, M. et al., "Collagen Shrinkage and Vessel Sealing," TissueLink Medical, Inc., Technical Brief #300, TissueLink, Dover, NH.
McClurken, M. et al., "Thermal Effect of Tissue Link™ Technology on liver," TissueLink Medical, Inc., Technical Brief #301, TissueLink, Dover, NH.
McMahon, C.J. et al., "Use of the Transseptal Puncture in Transcatherer Closure of Long Tunnel-Type Patent Foramen Ovale," Heart, Aug. 2002, 88:e3, (2 Pages).
Meier, B. et al., "Contemporary Management of Patent Foramen Ovale," Circulation, Jan. 7/14, 2003, pp. 5-9, American Heart Association.
Meier, B., "Patent Foramen Ovale-Beauty Spot of Health Threat," CardiologyRounds, pp. 1-8, vol. 5, Issue 10, Dec. 2001, Brigham and Women's Hospital, Boston, Massachusetts.
Nkomo, V., et al. "Patent Foramen Ovale Transcatheter Closure Device Thromboisis," Mayo Clin Proc., Oct. 2001, pp. 1057-1061, vol. 76, © May Foundation for Medical Education and Research.
NMT Medical, Inc. Brochure, "Cardioseal Septal Occlusion Systems," ML-0038.00, www.nmtmedical.com <http://www.nmtmedical.com>, Boston, MA (2 Pages).
NMT Medical, Inc. Brochure, "PFO Closure: Outcomes and Device Design Frequesently Asked Questions," ML-0116.00, pp. 1-4, www.nmtmedical.com <http://www.nmtmedical.com>, Boston, MA.
Overell, J.R. et al., "Interatrial Septal Abnormabilites and Stroke," Neurology, Oct. 2000 (2 of 2), vol. 55, pp. 1172-1179, © AAN Enterprises.
Patent Foramen Ovale [PFO], (1 Page).
Rosenbaum, M. et al., "An Exploratory Investigation of the Morphology and Biochemistry of Cellulite," Journal of the American Society of Plastic Surgeons, Jun. 1993, pp. 1934-1939, vol. 101, Issue 7, Lippincott,Williams & Wilkins. (Abstract Provided-2 Pages).
Ruiz, C. et al., "The Puncture Technique: A New Method for Transcatheter Closure of Patent Foramen Ovale," Catheterization and Cardiovascular Interventions, 2001, pp. 369-372, vol. 53, Wiley-Liss, Inc.
Schuchlenz, H. et al., "Transesophageal Echocardiography For Quantifying Size of Patent Foramen Ovale in patients With Cryptogenic Cerebrovascular Events," Stroke, Jan. 2003, p. 293-296, American Heart Association.
Schwerzmann, M. et al., "Percutaneous Closure of Patent Foramen Ovale Reduces the Frequency of Migraine Attacks," Neurology, Apr. 2004, (2 of 2), pp. 1399-1401, vol. 62, AAN Enterprises, Inc.
Shepard, S., "TissueLink's Hemostasis Device Stirs Interest of Local Surgeons," TissueLink, Nov. 7, 2003, Print Edition (3 Pages).
Silverglide, Surgical Technologies, inc., "What Makes SILVERGlide Non-Stick Bipolar Forceps Different." (1 Page).
Stuart, M., "Stroke Prevention: The Newest Frontier in Interventional Cardiology," Interventional Cardiology, Oct. 2003, p. 23-28, Windhover Information Inc.
Szili-Torok, T. et al., "Transseptal Left Heart Catheterisation Guided by Intracardiac Echocardiography," Heart, 2001, 86:e11, Dept. of Cardiology, Rotterdam, The Netherlands. (5 Pages).

The Thermage Procedure Brochure. (2 Pages).

Walsh, K.P. et al., "Transcatheter closure of patent foramen ovale Using the Amplatzer Septal Occluder to Prevent Recurrence of Neurological Decompression Illness in Divers," Heart 1999, pp. 257-261, vol. 81.

Wright, N. et al., "Denaturation of Collagen via Heating: An Irreversible Rate Process," Annual Review of Biomedical Engineering, 2002, pp. 109-128, vol. 4.

* cited by examiner

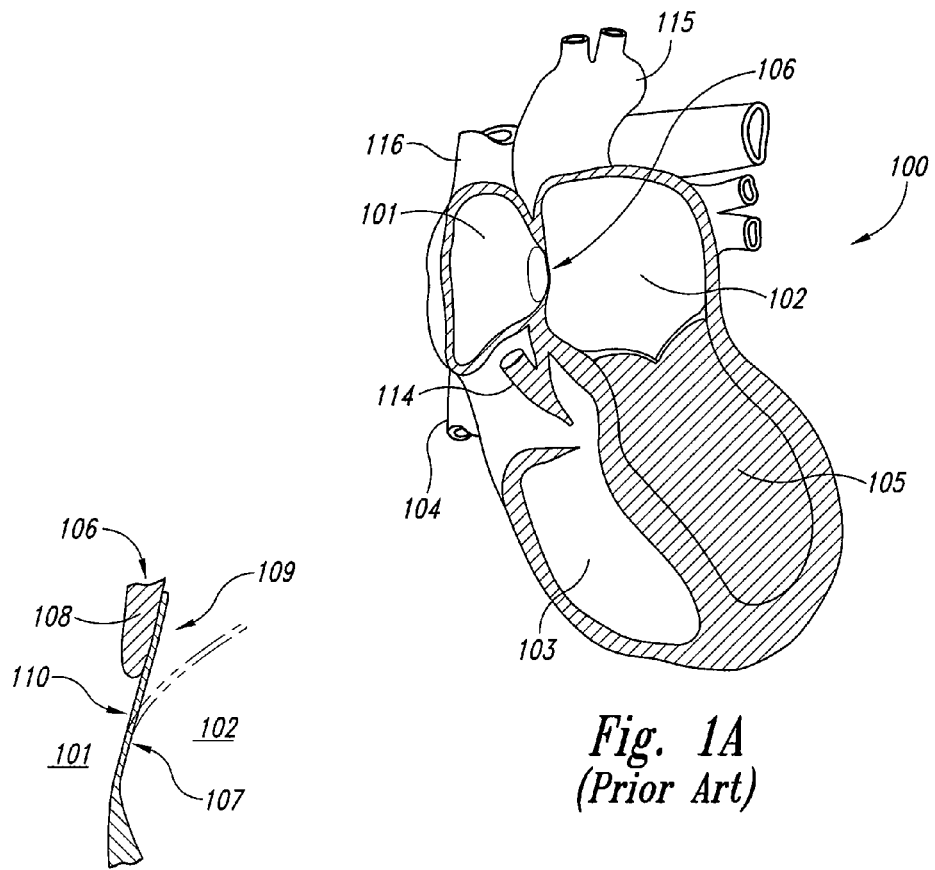
Fig. 1A
(Prior Art)
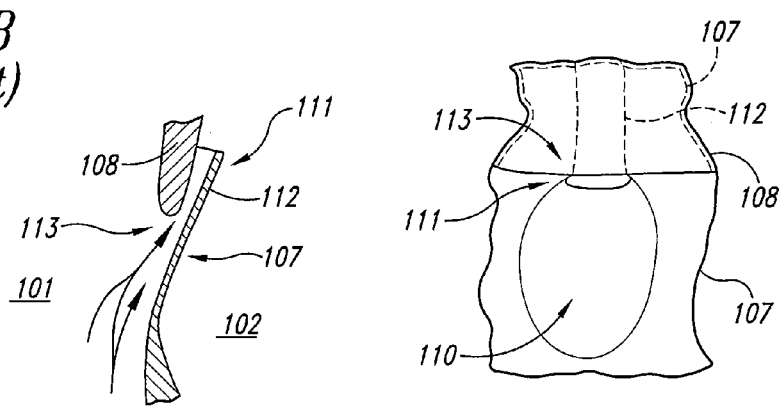
Fig. 1B
(Prior Art)
Fig. 1C
(Prior Art)
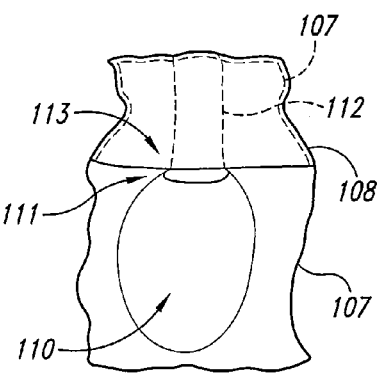
Fig. 1D
(Prior Art)

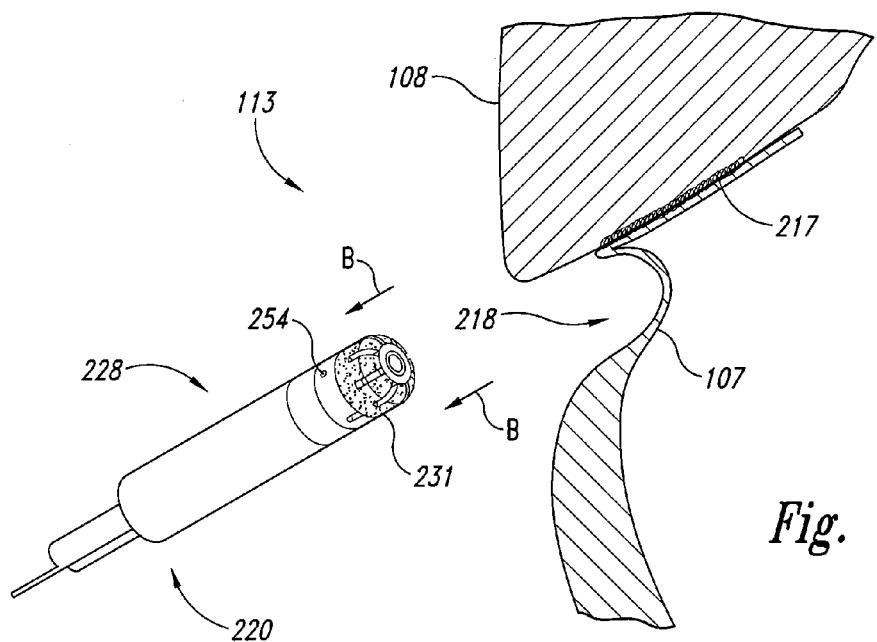
Fig. 2D
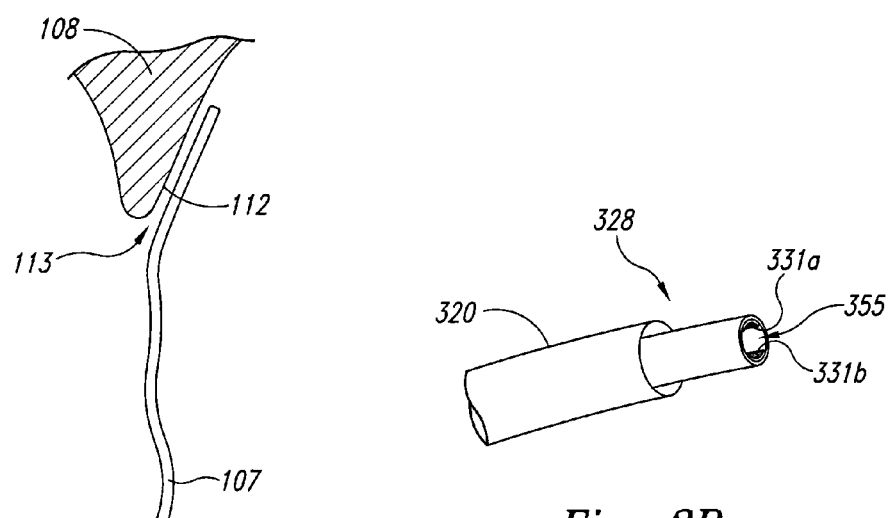
Fig. 3A
Fig. 3B

SYSTEMS AND METHODS FOR SHRINKING AND/OR SECURING CARDIOVASCULAR TISSUE

CROSS-REFERENCE TO RELATED APPLICATION

The present application claims priority to U.S. Provisional Application 60/617,247, filed Oct. 7, 2004 and incorporated herein by reference.

TECHNICAL FIELD

The present invention is directed generally to systems and methods for shrinking and/or securing cardiovascular tissue, including systems and methods for shrinking primum tissue.

BACKGROUND

The human heart is a complex organ that requires reliable, fluid-tight seals to prevent de-oxygenated blood and other constituents received from the body's tissues from mixing with re-oxygenated blood delivered to the body's tissues. FIG. 1A illustrates a human heart 100 having a right atrium 101, which receives the de-oxygenated blood from the superior vena cava 116 and the inferior vena cava 104. The de-oxygenated blood passes to the right ventricle 103, which pumps the de-oxygenated blood to the lungs via the pulmonary artery 114. Re-oxygenated blood returns from the lungs to the left atrium 102 and is pumped into the left ventricle 105. From the left ventricle 105, the re-oxygenated blood is pumped throughout the body via the aorta 115.

The right atrium 101 and the left atrium 102 are separated by an interatrial septum 106. As shown in FIG. 1B, the interatrial septum 106 includes a primum 107 and a secundum 108. Prior to birth, the primum 107 and the secundum 108 are separated to form an opening (the foramen ovale 109) that allows blood to flow from the right atrium 101 to the left atrium 102 while the fetus receives oxygenated blood from the mother. After birth, the primum 107 normally seals against the secundum 108 and forms an oval-shaped depression, i.e., a primum 107.

In some infants, the primum 107 never completely seals with the secundum 108, as shown in cross-sectional view in FIG. 1C and in a left side view in FIG. 1D. In these instances, a patency 111 often having the shape of a tunnel 112 forms between the primum 107 and the secundum 108. This patency is typically referred to as a patent foramen ovale or PFO 113. In most circumstances, the PFO 113 will remain functionally closed and blood will not tend to flow through the PFO 113, due to the higher pressures in the left atrium 102 that secure the primum 107 against the secundum 108. Nevertheless, during physical exertion or other instances when pressures are greater in the right atrium 101 than in the left atrium 102, blood can inappropriately pass directly from the right atrium 101 to the left atrium 102 and can carry with it clots or gas bubbles. Such constituents in the atrial system can pose serious health risks including hemodynamic problems, cryptogenic strokes, venous-to-atrial gas embolism, migraines, and in some cases even death.

Traditionally, open chest surgery was required to suture or ligate a PFO 113. However, these procedures carry high attendant risks, such as postoperative infection, long patient recovery, and significant patient discomfort and trauma. Accordingly, less invasive techniques have been developed. Most such techniques include using a transcatheter implantation of various mechanical devices to close the PFO 113. Such devices include the Cardia® PFO Closure Device, Amplatzer® PFO Occluder, and CardioSEAL® Septal Occlusion Device. One potential drawback with these devices is that they may not be well suited for the long, tunnel-like shape of the PFO 113. As a result, the implanted mechanical devices may become deformed or distorted and in some cases may fail, migrate, or even dislodge. Furthermore, these devices can irritate the cardiac tissue at or near the implantation site, which in turn can potentially cause thromboembolic events, palpitations, and arrhythmias. Other reported complications include weakening, erosion, and tearing of the cardiac tissues around the implanted devices.

Another potential drawback with the implanted mechanical devices described above is that, in order to be completely effective, the tissue around the devices must endothelize once the devices are implanted. The endothelization process can be gradual and can accordingly take several months or more to occur. Accordingly, the foregoing techniques do not immediately solve the problems caused by the PFO 113.

Still another drawback associated with the foregoing techniques is that they can be technically complicated and cumbersome. Accordingly, the techniques may require multiple attempts before the mechanical device is appropriately positioned and implanted. As a result, implanting these devices may require long procedure times during which the patient must be kept under conscious sedation, which can pose further risks to the patient.

BRIEF DESCRIPTION OF THE DRAWINGS

FIGS. 1A-1D illustrate a human heart having a patent foramen ovale (PFO) in accordance with the prior art.

FIGS. 2A-2D illustrate a catheter configured in accordance with an embodiment of the invention, and a method for using the catheter to draw cardiac tissue together and seal the cardiac tissue.

FIGS. 3A-3E illustrate methods and devices for shrinking the primum using suction in accordance with embodiments of the invention.

FIGS. 4A-4C illustrate methods and devices for shrinking the primum by clamping the primum in accordance with other embodiments of the invention.

DETAILED DESCRIPTION

A. Introduction

Figure 2A:
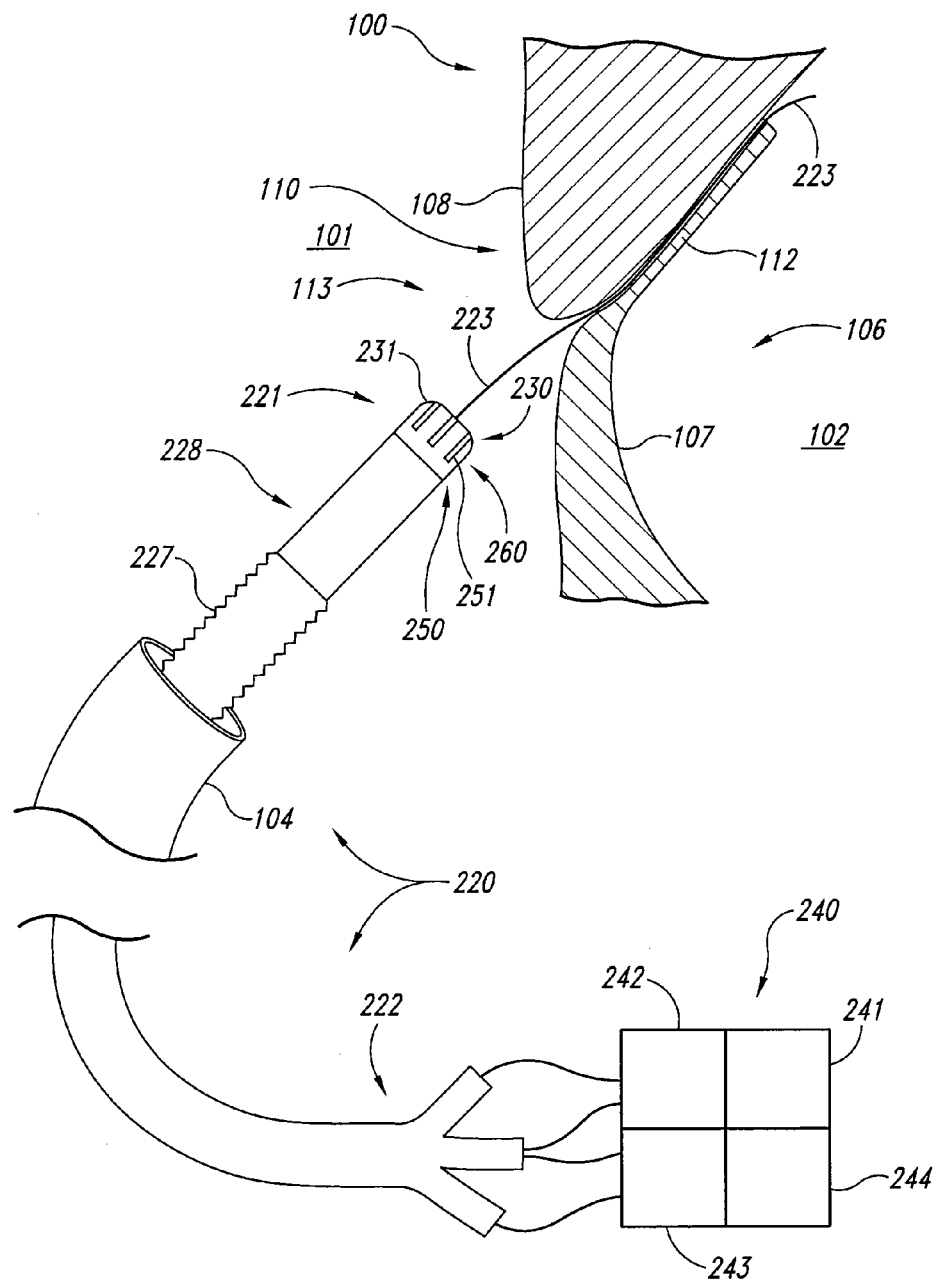

The present invention is directed generally to methods and devices for shrinking and/or tightening primum tissue, in combination with or independently of sealing a patent foramen ovale (PFO). For example, methods in accordance with particular embodiments of the invention can include drawing or gathering portions of the primum tissue together and fusing them. Well-known structures, systems, and methods often associated with these systems have not been shown or described in detail to avoid unnecessarily obscuring the description of the various embodiments of the invention. Those of ordinary skill in the relevant art will understand that additional embodiments of the invention may be practiced without several of the details described below.

A method in accordance with one aspect of the invention includes treating cardiac tissue that in turn includes a primum, a secundum adjacent to the primum, and a patent foraman ovale. The method can include shrinking the primum at a first location spaced apart from the patent foraman ovale, and at least partially sealing the patent foraman ovale by applying energy at a second location at least closer to the patent foraman ovale than the first location. In particular aspects, at least partially sealing the patent foraman ovale can include doing so without simultaneously shrinking the primum at the first location. For example, the primum can be shrunk before or after at least partially sealing the patent foraman ovale. The primum can be shrunk by heating the primum, drawing portions of the primum together and fastening them with a mechanical fastener, applying an adhesive to the primum, exposing the primum to a chemical agent, or directing ultrasonic energy to the primum.

A method for treating cardiac tissue in accordance with another aspect of the invention includes releasably tightening the primum at a first location spaced apart from the patent foramen ovale by drawing portions of the primum together. While the primum is releasably tightened, the method can further include at least partially sealing the patent foramen ovale by applying energy at a second location at least closer to the patent foramen ovale than the first location. The tension on the primum can be released after at least partially sealing the patent foramen ovale, allowing portions of the primum to move apart from each other. In particular aspects, tightening the primum can include clamping first and second portions of the primum together between first and second members, or applying a vacuum to a first section and a second section of the primum to fold at least one of the first and second sections against the other. At least partially sealing the patent foramen ovale can include inserting a portion of a catheter into the patent foramen ovale, drawing the primum and secundum into contact with each other by drawing a vacuum in a region adjacent to the primum and secundum, and applying RF energy to the primum and the secundum from an electrode position that is at least partially within the patency.

A method in accordance with still another aspect of the invention includes drawing a first section and a second section of the primum together, and applying energy to the first and second sections of the primum to fuse the first and second sections to each other. In further particular aspects, the first and second sections of the primum can be drawn together by applying a vacuum to the first and second sections, or by clamping the first and second sections between a first member and a second member to fold the first and second sections against each other. In yet another particular aspect, applying energy to the first and second sections of the primum includes applying energy at a first location of the primum spaced apart from a patent foramen ovale. The method can further comprise at least partially sealing the patent foramen ovale by applying energy at a second location at least partially within the patent foramen ovale.

B. Systems and Methods for Sealing a PFO

Aspects of the invention are directed to manipulating the primum tissue, as part of a procedure for treating a PFO, and/or as a stand-alone procedure (e.g., to treat an aneurysmal primum). FIGS. 2A-2D illustrate a catheter 220 and methods for using the catheter to treat the PFO, in accordance with several embodiments of the invention. FIGS. 3A-8 illustrate devices and methods for treating (e.g., shrinking) primum tissue adjacent to the PFO. As will be described below, the techniques and devices described in the context of each set of Figures can be used independently or in conjunction with each other.

Beginning with FIG. 2A, the catheter 220 can include a proximal end 222 coupleable to a control unit 240, and a distal end 221 having a working portion 228 configured to be placed in a patient's heart 100. A flexible portion 227 between the distal end 221 and the proximal end 222 can allow the catheter 220 to absorb stresses without disturbing the working portion 228. The distal end 221 can be inserted into the patient's heart 100 via the inferior vena cava 104 or another blood vessel. The catheter 220 can include a vacuum system 250 having vacuum ports 251 that are used to evacuate fluids (and/or solids, e.g., blood clots) in the regions surrounding the distal end 221. The force of the applied vacuum can accordingly draw portions of cardiac tissue toward each other and toward the catheter 220. The catheter 220 can also include an energy transmitter 230 (e.g., an electrode 231) that directs energy to the cardiac tissue portions to fuse the tissue portions together. A fluid supply system 260 can provide fluid to the working portion 228 to prevent the cardiac tissue from fusing to the electrode 231 or other portions of the energy transmitter 230 and/or to increase the penetration of the electrical field provided by the electrode 231.

The control unit 240 can control and/or monitor the operation of the energy transmitter 230, the vacuum system 250, and the fluid supply system 260. Accordingly, the control unit 240 can include an energy transmitter control/monitor 241, a vacuum control/monitor 242, and a fluid supply control/monitor 243. The control unit 240 can also include other controls 244 for controlling other systems or subsystems that form portions of, or are used in conjunction with, the catheter 220. Such subsystems can include but are not limited to, temperature and/or impedance detectors that determine the temperature and/or impedance of the cardiac tissue and can be used to prevent the energy transmitter 230 from supplying excessive energy to the cardiac tissue. The subsystems can also include current sensors to detect the current level of electrical signals applied to the tissue, voltage sensors to detect the voltage of the electrical signals, and/or vision devices that aid the surgeon or other practitioner in guiding the catheter 220. The control unit 240 can include programmable, computer-readable media, along with input devices that allow the practitioner to select control functions, and output devices (e.g., display screens) that present information corresponding to the operation of the catheter 220.

In a particular embodiment shown in FIG. 2A, the catheter 220 is inserted into the right atrium 101 to seal a PFO 113 that exists in the interatrial septum 106 between the right atrium 101 and the left atrium 102. Accordingly, the practitioner can first insert a guide wire 223 into the right atrium 101 and through the tunnel portion 112 of the PFO 113, using one or more suitable guide techniques. For example, the guide wire 223 can be moved inferiorly along the interatrial septum 106 until it "pops" into the depression formed by the primum 107. This motion can be detected by the practitioner at the proximal end 222 of the catheter 220. The tunnel 112 will typically be at least partially collapsed on itself prior to the insertion of the catheter 220, so the practitioner will likely probe the primum 110 to locate the tunnel entrance, and then pry the tunnel 112 open. Suitable imaging/optical techniques (e.g., fluoroscopic techniques, intracardiac echo or ICE techniques and/or transesophageal echocardiography or TEE) can be used in addition to or in lieu of the foregoing technique to thread the guide wire 223 through the tunnel 112. Corresponding imaging/optical devices can be carried by the catheter 220.

Figure 2B:
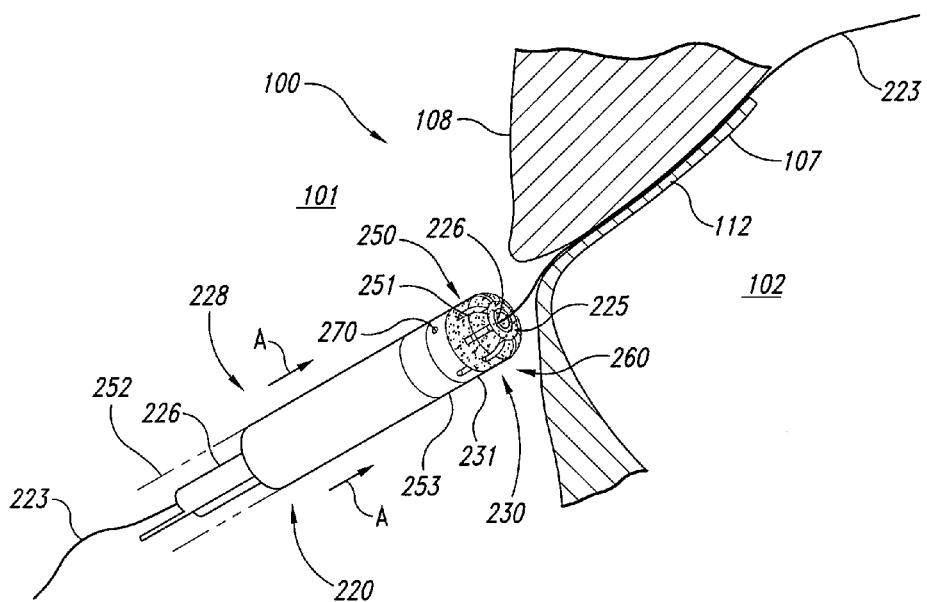

Referring next to FIG. 2B, the working portion 228 of the catheter 220 can be advanced along the guide wire 223, as indicated by arrows A. The working portion 228 can include a fluid manifold 253 for handling fluids supplied to and/or withdrawn from the heart 100, and an electrode holder 270 that supports the electrode 231. A guide wire holder 225 at the tip of the electrode 231 surrounds a guide wire conduit 226 through which the guide wire 223 passes, so as to keep the catheter 220 aligned along the guide wire 223.

As the catheter 220 is moved toward the tunnel 112, the practitioner can activate the vacuum system 250. The vacuum system 250 can include an internal vacuum passage coupled to vacuum ports 251 formed in the exterior surface of the electrode 231. Accordingly, the vacuum system 250 can draw in fluid from the region immediately surrounding the distal end 221 of the catheter 220 through the vacuum ports 251. The fluid drawn through the vacuum ports 251 can be evacuated from the patient's body via a vacuum line 252 that surrounds the guide wire conduit 226.

The catheter 220 can have a diameter of from about 3 to about 5 millimeters (9-15 French) and in one embodiment, a diameter of about 4 millimeters. This size allows the catheter 220 to fit at least partially into most (clinically symptomatic) tunnels 112. The practitioner can select smaller catheters 220 for very small tunnels 112. For larger tunnels 112, the practitioner can use larger catheters 220, or multiple catheters 220 in parallel, or multiple, sequential fusion operations with a single catheter 220. As described below, using a catheter having a size on the same order as the size of the tunnel 112 (e.g., a catheter occupying at least 40% of the tunnel 112) can allow the catheter 220 to draw the primum 107 and the secundum 108 into close contact with each other when the catheter 220 is inserted into the PFO tunnel 112.

Figure 2C:
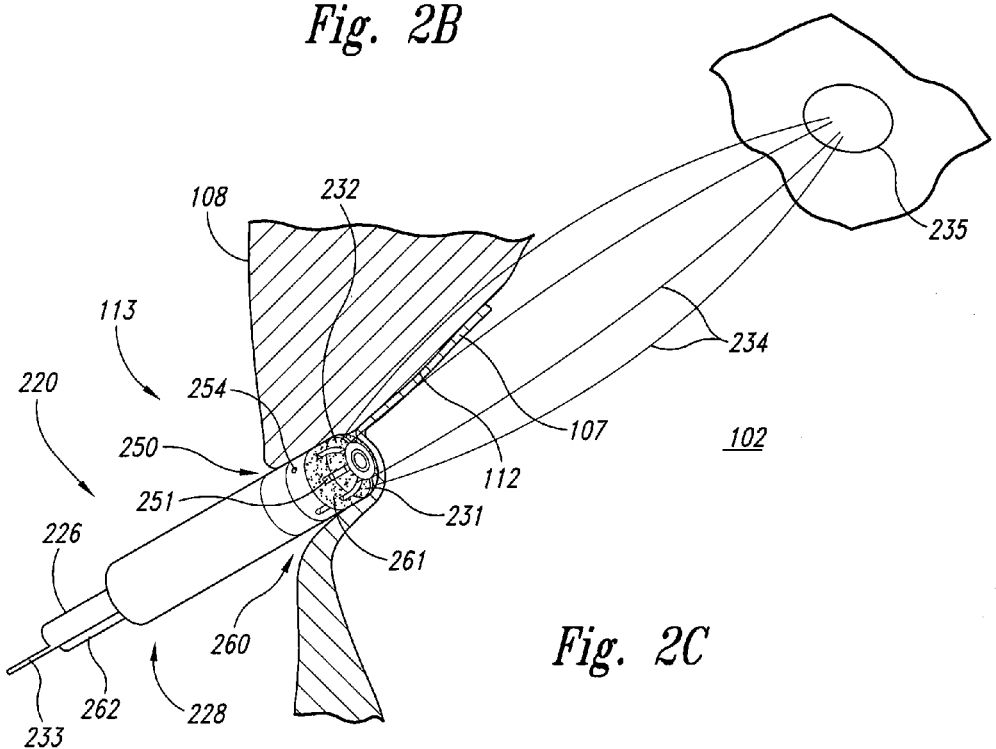

FIG. 2C illustrates the catheter 220 after the working portion 228 has been inserted part way into the tunnel 112. As the catheter 220 advances into the tunnel 112, an outer periphery 232 of the electrode 231 begins to contact both the primum 107 and the secundum 108. At the same time, the vacuum system 250 continues to draw liquid through the vacuum ports 251 and also through a locating port 254. Accordingly, the cardiac tissue will begin to seal or clamp against the vacuum ports 251. The practitioner can continue to insert the catheter 220 until the locating port 254 is covered by cardiac tissue, optionally by temporarily reducing the vacuum pressure to allow for easier movement of the catheter 220. At this point, the catheter 220 has been inserted into the tunnel 112 by a target distance, preselected to provide good sealing performance. The target distance can be from about 1 to about 15 millimeters for typical PFOs 113. With the catheter at this position, the tunnel 112 is completely collapsed on itself, causing the primum 107 to coarct with (e.g., clamp against and/or conform closely with) the secundum 108. The primum 107 can also stretch and coarct with the periphery 232 of the electrode 231. Accordingly, the catheter 220 is secured in a position relative to the PFO 113, and the guide wire 223 (FIG. 2B) can be withdrawn from the tunnel 112. In another embodiment, the guide wire 223 can remain in the tunnel 112 during the PFO sealing process. The vacuum provided by the catheter 220 can optionally also be used to remove blood clots from the PFO 113, if desired.

The level of vacuum applied by the catheter 220 can be varied during the insertion process and/or other processes.

For example, the practitioner can set the vacuum level to a relatively low differential pressure to partially secure the cardiac tissue while the guide wire 223 (FIG. 2B) is in the tunnel 112. The practitioner can increase the differential pressure after the guide wire 223 is removed to more completely secure the catheter 220.

During the foregoing insertion process, the catheter 220 can have any rotational position relative to the guide wire 223 (FIG. 2B) without affecting performance. This simplifies the insertion task because the practitioner need not track or adjust the rotational orientation of the catheter 220. During the foregoing insertion process, the practitioner can also receive positive feedback indicating that the catheter 220 is secured within the tunnel 112. For example, the practitioner can observe a decrease in the rate at which fluid is withdrawn from the patient (via the vacuum system 250) when the catheter 220 seals the tunnel 112. In particular examples, the practitioner can observe a fluid drip, or (for higher flowrates) a flowmeter, or fluid flow through translucent tubing, or another monitoring device. The practitioner can also observe an increase in the differential pressure pulled by the vacuum system 250 when the tunnel 112 collapses on itself and against the vacuum ports 251. For example, the practitioner can observe a vacuum gauge.

Prior to providing electrical power to the electrode 231, the practitioner can activate the fluid supply system 260. The fluid supply system 260 can pump fluid through a fluid supply line 262 and through pores 261 located at the working portion 228 of the catheter 220 (e.g., in a peripheral surface 232 of the electrode 231). The fluid can be selected to be electrically conductive so as not to interfere with the transmission of electrical signals to the cardiac tissues by the electrode 231. For example, the fluid can be selected to include a saline solution having normal concentration (e.g., 0.9%) or higher concentrations (e.g., 3%-4%). The flow rate of the fluid can be selected to form a thin film of fluid between the electrode 231 and the adjacent cardiac tissue. The flow rate can be low enough to form a thin fluid film that does not interfere with the ability of the vacuum system 250 to hold the primum 107 and the secundum 108 together. In this manner, the vacuum system 250 and the fluid supply system 260 can be operated in conjunction with each other to: (a) secure the electrode 231 relative to the PFO 113, (b) secure the primum 107 and the secundum 108 against each other while they are fused together, and (c) prevent or at least restrict fusion between the cardiac tissue and the electrode 231. Representative flow rates and pressures are described below with reference to FIG. 3B.

In a particular embodiment, the fluid supply system 260 can be activated for about 5 seconds before activating the electrode 231. In other embodiments, this time period can have different values. In any of these embodiments, the fluid can perfuse the adjacent cardiac tissue with electrically conducting ions to increase the efficiency with which electrical energy is transmitted into and/or through the tissue. For purposes of illustration, a single supply line 262 is shown in FIG. 2C. In other embodiments, the fluid system 260 can supply multiple fluids independently through multiple supply lines. The multiple fluids can have different properties, and can be electrically isolated from each other via the multiple supply lines.

The configuration shown in FIG. 2C employs a monopolar electrode 231 coupled to an electrical lead 233. Accordingly, the practitioner places a return electrode 235 remote from the treatment site to provide a conductive return path for electrical current provided by the electrode 231. Most conventional return electrodes are placed against the patient's buttocks and have a large surface area so as to reduce the likelihood for burning. Unlike these conventional return electrodes, the return electrode 235 can be relatively small (e.g., about four inches in diameter), and can be placed superior to the PFO 113 (e.g., superior to the patient's heart 100). When a current is applied to the electrode 231, the resulting electrical field forms flux lines 234 extending generally between the electrode 231 and the return electrode 235. For purposes of illustration, only those flux lines 234 extending more or less directly between the electrode 231 and the return electrode 235 are shown in FIG. 2C. Accordingly, the flux lines 234 can be aligned with the interface between the primum 107 and the secundum 108. The electrical current can therefore fuse the primum 107 to the secundum 108 along at least a portion of the length of the tunnel 112. The current path in the embodiment extends into a bloody field of the left atrium 102 after passing through the primum 107. For example, about 10% to about 70% of the electrical current can pass through the left atrial blood. Current may preferentially flow toward the left atrium, due to the thin nature of the primum 107 and/or the quality of the vacuum seal with the electrode 231. In other embodiments, the return electrode 235 can have other locations relative to the heart 100, e.g., offset laterally from the heart 100. In still further embodiments, the configuration can include a bipolar or a bipolar/monopolar electrode arrangement, as is disclosed in pending U.S. application Ser. No. 11/004,634, filed Dec. 12, 2004 and incorporated herein by reference.

The electrical current provided to fuse the cardiac tissue is provided at a relatively high frequency to create an RF energy field. The current and power can be varied and controlled in myriad manners, some of which are discussed later with reference to FIG. 3B. In a typical case, the power provided to fuse the tissue can have a value of about 30 watts, which can be returned via the (relatively small) return electrode 235 without burning the patient. The temperature of the cardiac tissue can be raised to from about 57° C. to about 100° C. to promote tissue fusing.

Referring now to FIG. 2D, the working portion 228 of the catheter 220 can be withdrawn from the PFO 113 (as indicated by arrows B) after the fusion process has been completed. The fusion process results in a seal 217 between the primum 107 and the secundum 108. The seal 217 is formed when, due to the elevated temperature resulting from the electrical field produced by the electrode 231, the cell walls of the cardiac tissue become disrupted. The tissue proteins, including collagen and elastin, are denatured, forming a coagulum. The collagen in the cells also tends to shrink under heat, which can further act to bind the tissues together, e.g., by cross-linking or entangling the coagulum. Intra- and intercellular fluids (e.g., denatured blood proteins, including albumin) can also mix, forming a type of "biological glue." The sealing process can be enhanced by this protein glue.

The seal 217 can be made to withstand significant pressures, at least approximately the same as the maximum pressures typically encountered between the left and right atria of the heart. For example, the seal 217 can withstand a pressure of about 5.0 mm Hg. The seal 217 need not extend for the entire length of the tunnel 112, which can be from about 5 mm to about 15 mm. In fact, in many cases, it may be desirable to leave the distal opening of the tunnel (e.g., the scupper valve, which opens into the left atrium) open. However, in many cases it is desirable to seal the entire width of the tunnel 112 (generally perpendicular to the plane of FIG. 2D), which can be from about 2 mm to about 18 mm. Accordingly, it may be desirable to have the flux lines 234 (FIG. 2C) extend widthwise as well as lengthwise into the tunnel 112. One way to achieve this end is to perfuse the region around the electrode 231 with conductive fluid, as described above, so as to increase the effective size of the electrode in the widthwise direction. In a particular embodiment, the power provided to the electrode 231 in combination with liquid perfusion and/or other factors causes the electrical field strength to be high enough to fuse the tissue at distances of at least 20% greater than the diameter of the catheter 220. In some situations, even if the seal 217 is initially incomplete, the body's own healing processes may act to complete the seal over time. Accordingly, the foregoing methods need not necessarily complete the entire seal during the surgical procedure.

After the catheter 220 is withdrawn from the sealed area, a small concavity 218 can remain in the right atrial septum. However, in light of the integrity of the seal 217, the concavity 218 can have little or no impact on the normal flow of blood from the right atrium 101 to the right ventricle. The integrity of the seal can be verified using any of a number of known techniques, including the use of contrast agents and/or bubbles.

C. Systems and Methods for Shrinking/Tightening a Primum

In some instances, the primum 107 (which is generally quite thin) can be loose, or floppy, or otherwise aneurysmal or partially aneurysmal, as is illustrated schematically in FIG. 3A. Current data indicate that patients with both (a) an aneurysmal primum 107 and (b) a PFO 113, may be six to seven times as likely to have a stroke as patients having only a PFO 113. For this reason alone, it may be beneficial to tighten the primum 107. In addition, it may in some cases be difficult to maintain a tight vacuum seal between the electrode 231 (described above) and the primum 107 if the primum 107 is flopping about excessively. Accordingly, tightening the primum 107 can have the additional benefit of improving the efficiency of the process for sealing the PFO described above. Still further, it may be beneficial to shrink a patient's aneurysmal primum 107, even if the patient does not have a PFO 113.

FIG. 3B through FIG. 8 illustrate devices and techniques for tightening the primum 107 in accordance with several embodiments of the invention. Referring first to FIG. 3B, a catheter 320 in accordance with one embodiment of the invention can include a working portion 328 having a vacuum channel 355 through which a vacuum may be drawn. The working portion 328 can also include multiple electrodes 331 (two are shown in FIG. 3B as electrodes 331a, 331b) located in the vacuum channel 355. In a particular aspect of this embodiment, the electrodes 331 can have generally semi-cylindrical shapes, and in other embodiments, the electrodes 331 can have other shapes. The electrodes 331 can be coupled to different potentials to operate in a bipolar fashion.

Figure 3C:
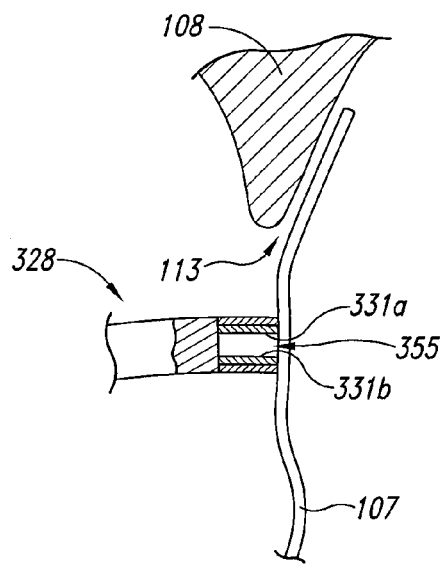
Figure 3D:
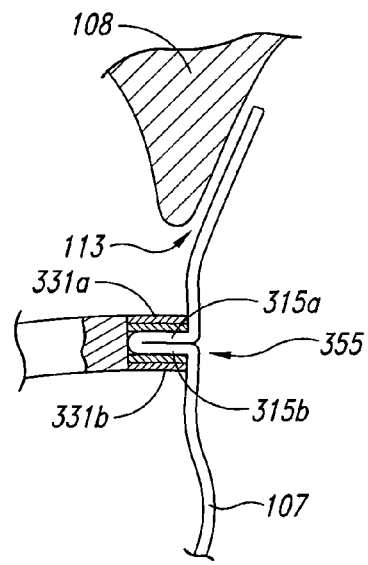
Figure 3E:
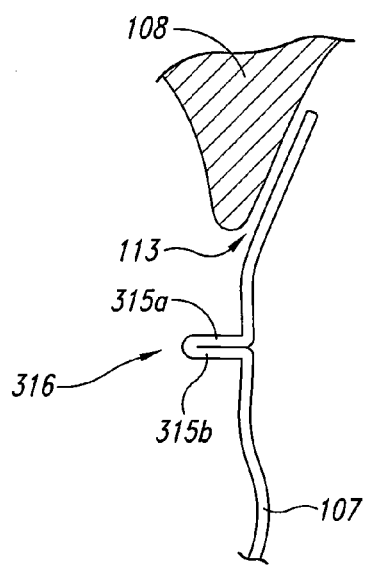

As shown in FIG. 3C, the working portion 328 can be positioned against the primum 107, so the vacuum channel 355 faces toward the right atrial surface of the primum 107. At this point, a vacuum can be drawn on the vacuum channel 355 and, as shown in FIG. 3D, part of the primum 107 can be drawn into the vacuum channel 355. For example, a first section 315a and a second section 315b can be drawn into the vacuum channel 355 and can be folded against each other within the vacuum channel 355. When power is applied to the electrodes 331, (e.g., in a varying manner to produce RF energy) the first and second sections 315a, 315b can fuse together, as shown in FIG. 3E, forming a fused portion 316. The amount of energy applied to the electrodes 331 can be metered, and can have a value in the range of from about 5 Joules to about 100 Joules. By gathering the first and second sections 315a, 315b together and drawing them away from the general plane of the primum 107, the primum 107 can be tightened, as is also shown schematically in FIG. 3E. In some embodiments, this process can be carried out at a single location of the primum 107. In other embodiments, for example, when the primum 107 has a significant degree of looseness, the foregoing process can be performed at multiple locations of the primum 107. In any of these embodiments, the location at which the fused portion 316 is formed can be spaced apart from the PFO 113. Accordingly, the presence of one or more fused portions 316 will tend not to interfere with the process of introducing electrodes or other energy sources into the PFO 113 to seal the PFO 113 (as described above with reference to FIGS. 2A-2D).

When the primum 107 is tightened in order to improve the seal between the PFO 113 and a vacuum-assisted PFO sealing device inserted into or near the PFO 113, the process of tightening the primum 107 may be performed prior to the process of sealing the PFO 113. Accordingly, the method can include shrinking the primum at one or more first locations spaced apart from the PFO 113, and then at least partially sealing the PFO 113 by applying energy (e.g., RF energy) at a second location at least closer to the PFO 113 than the first location (e.g., at a location within the PFO). In other embodiments, for example, when tightening the primum 107 is not required or particularly beneficial to the process for sealing the PFO 113, the primum 107 can be tightened after the PFO 113 is sealed. In still further embodiments, for example, when the patient does not have a PFO 113, or when the PFO 113 is determined to be of negligible consequence, the primum 107 can be tightened or shrunk without providing any treatment specifically directed to a PFO.

In other embodiments, other techniques can be used to shrink or tighten the primum 107. For example, referring now to FIG. 4A, a catheter working portion 428 can include a clamping device 480a for tightening the primum 107. In one aspect of this embodiment, the clamping device 480a can include a first member 481a and a second member 481b coupled at a pivot joint 482. Each of the first and second members 481a, 481b can include teeth, other sharpened projections, and/or other friction-enhancing features that allow the first and second members 481a, 481b to grasp the primum 107. The first and second members 481a, 481b can be electrically conductive and can accordingly be coupled to an electrical power source to deliver energy to the primum 107.

Referring next to FIG. 4B, the first and second members 481a, 481b have been placed in contact with the primum 107 and have been pivoted toward each other to clamp a first section 315a of the primum 107 against a second section 315b. When electrical power is delivered to the first and second members 481a, 481b, they can operate as bipolar, RF electrodes and can fuse the first and second portions 315a, 315b to each other, forming a fused portion 416. As described above with reference to FIGS. 3A-3E, this technique can be repeated at multiple locations spaced apart from the PFO 113 to provide the desired level of shrinking and/or tightening of the primum 107.

Figure 4C:
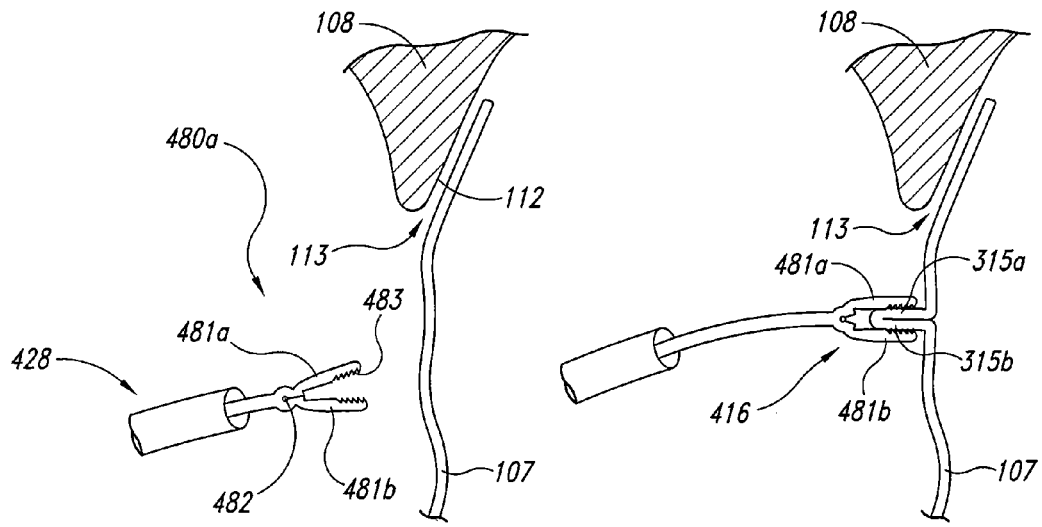
Figure 4C:
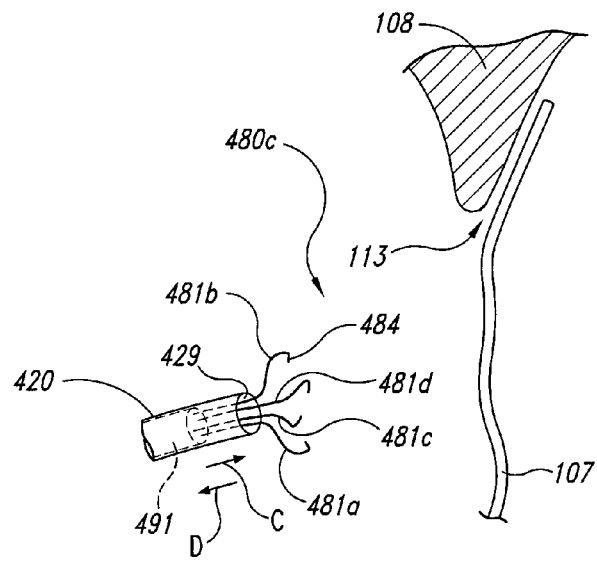

FIG. 4C illustrates a clamping device 480c configured in accordance with another embodiment of the invention. In one aspect of this embodiment, the clamping device 480c can include four members 481 (shown as first, second, third and fourth members 481a-481d), each connected to an applicator 491. Each of the members 481 can include a barb 484 or other sharpened projection that is positioned to grasp the primum 107 (FIG. 4A). The members 481 can be formed from a flexible, resilient, electrically conductive material. Accordingly, the members 481 can initially be stowed in a collapsed state within a catheter 420, and can then be deployed outwardly as indicated by arrow C for contact with the primum 107. Once in contact with primum 107, the members 481 can be withdrawn back into the catheter 420 as indicated by arrow D to both grasp the primum 107 and draw portions of the primum 107 together. Once the primum portions have been drawn together, electrical current can be supplied to the members 481 in a bipolar manner to fuse the grasped tissue. By gathering up and fusing the tissue, the primum 107 can be tightened, as was discussed above with reference to FIGS. 3A-4B.

Figure 5A:
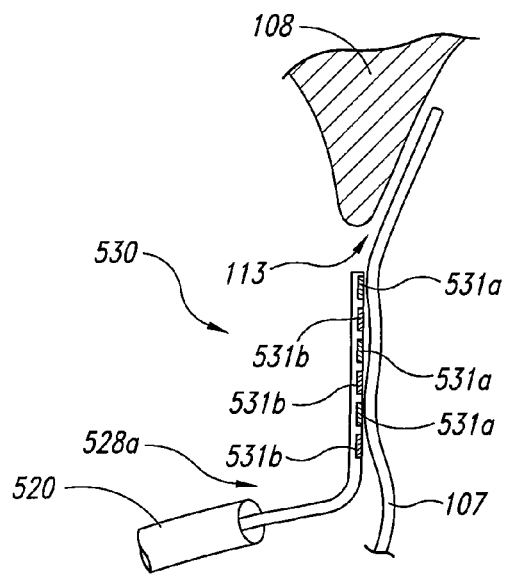
FIG. 5A-5C illustrate methods and devices for shrinking the primum using electrodes in accordance with still further embodiments of the invention.
Figure 5B:
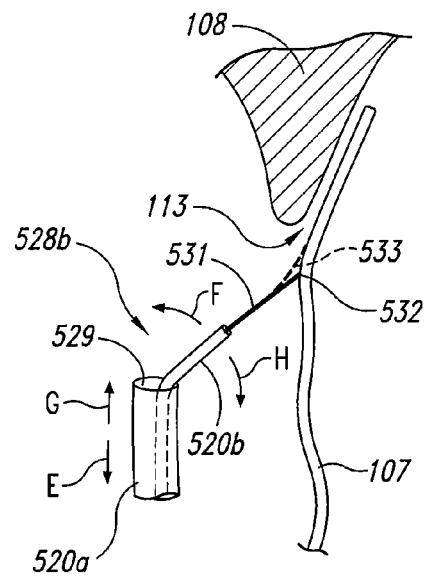
Figure 5C:
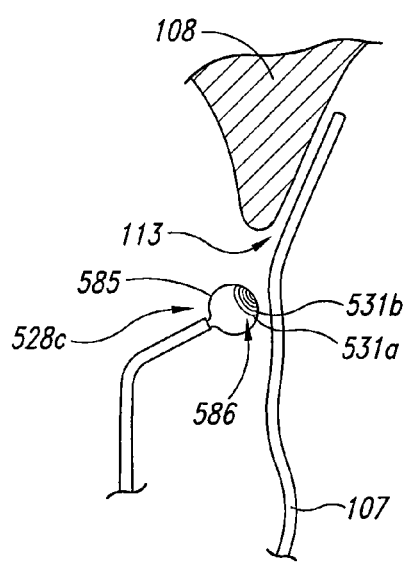

FIGS. 5A-5C illustrate electrodes suitable for shrinking the primum and configured in accordance with still further embodiments of the invention. For example, referring first to FIG. 5A, a catheter 520 can house a working portion 528a that includes an electrode member 530 having multiple electrodes 531 (shown in FIG. 5A as anodal electrodes 531a and cathodal electrodes 531b). The electrodes 531 can be positioned along one longitudinal face of the electrode member 530, and can be deployed from the catheter 520 so as to rest against the primum 107. RF energy delivered by the electrodes 531 can heat the adjacent primum tissue, causing the tissue to shrink and tighten the primum 107. By moving the electrode member 530 over the surface of the primum 107, this technique can be repeated at multiple locations to increase the extent to which the primum 107 is tightened.

FIG. 5B schematically illustrates a system that includes an outer catheter 520a housing a deployable inner catheter 520b, which in turn houses a deployable electrode 531. The electrode 531 can include a relatively thin conductive member having an exposed end surface 532 and/or an exposed side surface 533 that can transmit monopolar RF energy to the primum 107. Other portions of the electrode 531 can be insulated with a dielectric material to reduce the amount of electrical current that is not directed to the primum 107. In one aspect of this embodiment, the end surface 532 of the electrode 531 can be placed in contact with the primum and RF energy can be directed from the electrode 531 in a monopolar fashion to heat and shrink the primum 107. A return electrode is positioned elsewhere on the patient's body, for example, in a manner generally similar to that described above with reference to FIG. 2C. In another embodiment, the side surface 533 can be laid against the primum 107 (as shown by dashed lines), and current can be supplied in a monopolar fashion to shrink a potentially larger portion of the primum 107.

In either of the foregoing embodiments, a working portion 528b of the system, including the electrode 531, can be moved over the primum 107 to shrink the primum 107 at several locations, without necessarily moving the outer catheter 520a. For example, the inner catheter 520b can include a preformed bend, but can be generally resilient so that when it is straightened and then released, it tends to return to its bent position. As a result, the inner catheter 520b (and the electrode 531) can be drawn into the outer catheter 520a as indicated by arrow E, forcing the inner catheter 520b against an inner wall 529 of the outer catheter 520a, and straightening the inner catheter 520b as indicated by arrow F. This motion "scans" the electrode 531 in an arcuate manner, also indicated by arrow F. When the inner catheter 520b is moved outwardly from the outward catheter 520a (as indicated by arrow G), the inner catheter 520b can return to its bent position, scanning the electrode 531 in the opposite direction as indicated by arrow H. As a result, the outer catheter 520a can remain on station, while the electrode 531 scans over the primum 107 to heat and shrink the primum 107 at multiple different locations.

FIG. 5C illustrates a working portion 528c that includes a deployable, inflatable member 585. The inflatable member 585 can include a balloon-like device having a face region 586 that carries one or more electrodes 531 (two bipolar electrodes are shown in FIG. 5C as a first electrode 531a and a second electrode 531b). The electrodes 531a, 531b can be arranged in concentric spirals to provide for uniform RF heating of the primum 107. The inflatable member 585 can be constructed using techniques known to those of ordinary skill in the relevant art, and inflated using saline or other suitable fluids, also known to those of ordinary skill in the relevant art.

Figure 6:
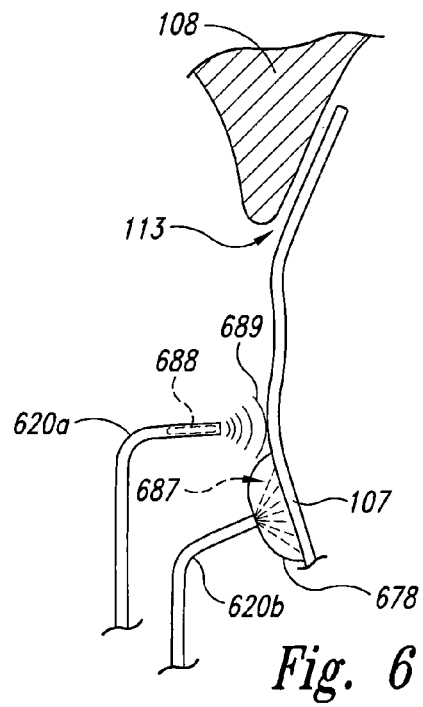
FIG. 6 illustrates methods and devices for shrinking the primum using other energy sources and/or mechanical arrangements in accordance with yet further embodiments of the invention.

FIG. 6 schematically illustrates two further methods for shrinking the primum 107. For purposes of illustration, both methods are illustrated together in FIG. 6, though it will be understood by those of ordinary skill in the relevant art that in most instances, one method or the other would be used to shrink the primum 107 of a particular patient. In one method, shear wave ultrasonic energy 689 can be delivered to the primum 107 to heat and shrink the primum tissue. Accordingly, a catheter 620a can be positioned proximate to the primum 107, and can deliver the ultrasonic energy 689 via an ultrasonic transmitter 688. In another embodiment, a catheter 620b can be positioned proximate to the primum 107 and can deliver a chemical agent 687 at least proximate to the primum 107 to shrink the primum tissue. For example, the chemical agent 687 can be selected to safely shrink the primum 107, in a manner generally similar to that used to shrink varicose veins or esophageal varices using ethanol. In another embodiment, the chemical agent 687 can include an adhesive that may be used to bind portions of the primum 107 together. In either embodiment, a membrane 678 can confine the chemical agent 687 to a selected region of the primum 107, or other techniques (e.g., a hypodermic needle carried by the catheter) can be used to precisely target the delivery of the chemical agent 687. Any of the foregoing vacuum and/or mechanical techniques drawing the tissue portions together can be used to draw or gather the tissue portions together prior to applying the adhesive.

Figure 7A:
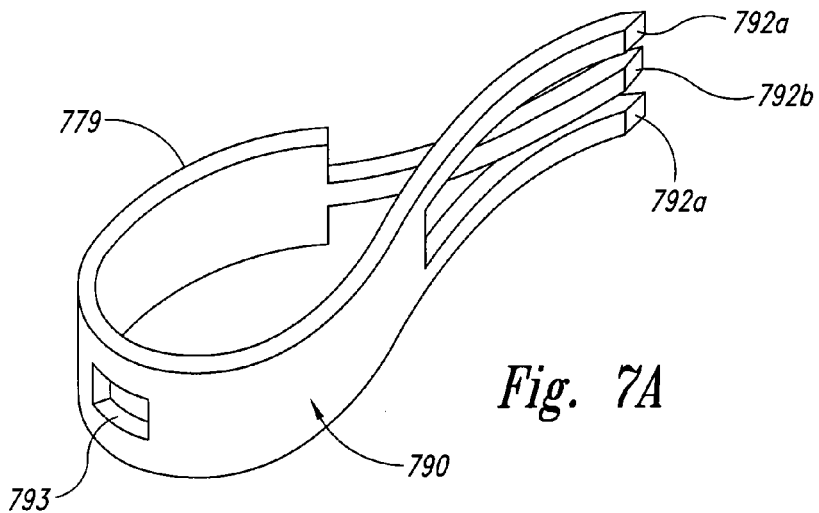
FIGS. 7A-7D illustrate methods for mechanically tightening the primum in accordance with further embodiments of the invention.
Figure 7B:
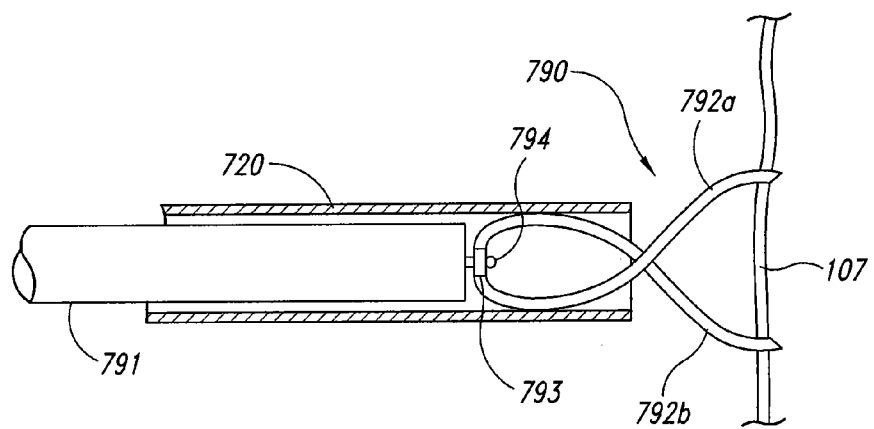
Figure 7C:
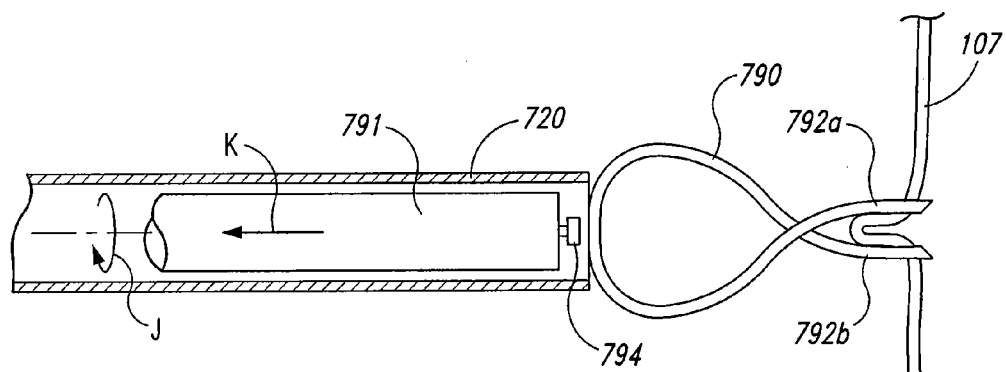
Figure 7D:
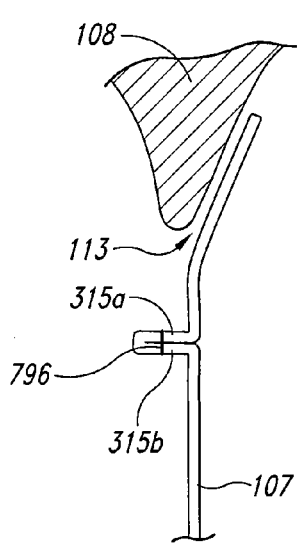

FIGS. 7A-7C illustrate a mechanical clip 790 and a method for installing the clip in a manner that tightens the primum 107. The clip 790 can include a resilient, flexible material that tends toward the shape shown in FIG. 7A. The clip 790 can include multiple arms 792 (shown in FIG. 7A as two first arms 792a and an intermediate second arm 792b) that extend from a connecting portion 779. A slot 793 can be positioned in the connecting portion to releasably attach the clip 790 to an applicator during a deployment operation.

FIG. 7B illustrates the clip 790 releasably attached to an applicator 791, which is in turn positioned within a catheter 720. A T-shaped toggle 794 (viewed from the side in FIG. 7B) can be inserted into the slot 793 of the clip 790 and rotated to secure the clip 790 to the applicator 791. When the clip 791 is partially deployed from the working portion 728 (with the connecting portion 779 still compressed by the walls of the working portion 728), the second arm 792b and the first arms 792a are forced away from each other. When the clip 790 completely exits the working portion 728, as shown in FIG. 7C, the second arm 792 and the first arms 792a tend to spring toward each other, clamping the first and second sections of primum tissue 315a, 315b together. The applicator 791 can then be rotated about its longitudinal axis (arrow J) and drawn into the catheter 720 (arrow K) to disengage the toggle 794 from the clip 790.

In other embodiments, other mechanical devices can be used to secure the first section 315a to the second section 315b. For example, referring now to FIG. 7D, a surgical stitch 796 can be used to secure the two tissue sections 315a, 315b to each other. Multiple stitches may be used to tighten the primum 107 at multiple locations.

Figure 8:
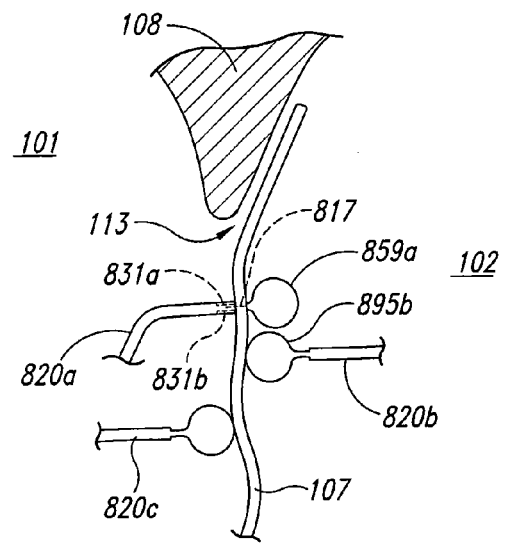
FIG. 8 illustrates methods and devices for at least temporarily tightening the primum by applying pressure from the left atrium in accordance with still further embodiments of the invention.

Referring next to FIG. 8, the primum 107 can, in some instances, be temporarily stretched or tightened while the PFO 113 is being sealed. After the PFO 113 has been sealed, the tightening force applied to the primum 107 can be released. For example, a right atrial catheter 820a can be positioned proximate to the primum 107 and can deploy an inflatable member 895a through a transseptal puncture 817 in the primum 107. When the inflatable member 895a is inflated (and, optionally, when the right atrial catheter 820a is drawn away from the primum 107), the primum 107 can be releasably stretched while the PFO 113 is being sealed. Optionally, the right atrial catheter 820a can also include bipolar electrodes 831 (shown as a first electrode 831a and a second electrode 831b) to permanently shrink the primum 107. However, if the primum 107 need not be permanently shrunk, the inflatable member 895a can be deflated after the PFO 113 has been sealed and the primum 107 can return to its original shape. An advantage of this arrangement is that it can allow the practitioner to temporarily stretch the primum 107 while sealing the PFO 113, but it need not require the patient to undergo additional permanent tissue manipulation if such manipulation is not necessary.

For purposes of illustration, a left atrial catheter 820b is shown in the same Figure as the right atrial catheter 820a, but it will be understood by those of ordinary skill in the relevant art that in most instances, one or the other catheter will be used to treat a particular patient. The left atrial catheter 820b can be introduced into the left atrium and can include an inflatable member 895b that contacts the primum 107 and, by applying pressure to the primum 107, stretches the primum 107. If the stretching is to be temporary, the inflatable member 895b need not have additional features, and can simply be deflated after the PFO 113 is sealed. In another embodiment, the inflatable member 895b can include an arrangement of electrodes generally similar to that described above with reference to FIG. 5C to permanently shrink and/or tighten the primum 107. In still further embodiments, a right atrial catheter 820c having a configuration generally similar to that of the left atrial catheter 820b can be located in the right atrium (instead of the left atrium) to apply releasable tension to the primum from the right atrium.

In other embodiments, other devices can be used to temporarily shrink and/or tighten the primum 107. For example, the clamping devices shown in FIGS. 4A-4C can be used (without activating the electrodes) to releasably tighten the primum. In still further embodiments, other techniques can be used to provide this function.

One feature of several of the embodiments described above is that they include shrinking or tightening the primum 107 in connection with a procedure for sealing the PFO 113. An advantage of this arrangement is that shrinking the primum 107 can allow certain techniques (e.g., those that include applying a vacuum to the PFO tissue) to have an increased likelihood of success. Accordingly, these techniques can be used in a temporary fashion only while the PFO is being sealed, or in a permanent fashion to provide long-term improvement of an initially aneurysmal primum.

Another feature of at least some of the foregoing embodiments is that they can, in at least some instances, eliminate the need for sealing a PFO. For example, a PFO can operate in the manner of a valve, and may tend to open or crack only when the pressure in the right atrium exceeds the pressure in the left atrium. Tightening the primum can cause the cracking pressure of the PFO to increase, even if the pressure in the right atrium exceeds the pressure in the left atrium by some amount. In at least some cases, tightening the primum can increase the effective cracking pressure of the PFO enough that (a) the chances of the PFO opening and allowing emboli to pass to the left atrium are significantly reduced, so that (b) the need for sealing the PFO can be eliminated.

Yet another feature of several embodiments described above is that they can be used to shrink the primum independently of whether or not the patient has a PFO 113. Accordingly, many of the foregoing techniques can be used to address a potentially harmful aneurysmal condition in patients that do not also have a PFO.

From the foregoing, it will be appreciated that specific embodiments of the invention have been described herein for purposes of illustration, but that various modifications may be made without deviating from the invention. For example, the electrodes, mechanical devices, inflatable members and/or other components described above can have configurations different than those shown in the Figures in other embodiments. The electrodes can be configured to heat the primum by direct conduction (in the manner of an electric stove element) rather than by delivery of RF energy. The PFO may have different configurations in other embodiments. For example, the left atrial end of the PFO may be closed in some embodiments. Aspects of the invention described in the context of particular embodiments may be combined or eliminated in other embodiments. For example, the catheter working portion 328a shown in FIG. 3A can have a bent shape similar to that of the working portion 528c shown in FIG. 5C. Although advantages associated with certain embodiments of the invention have been described in the context of those embodiments, other embodiments may also exhibit such advantages. Additionally, none of the foregoing embodiments need necessarily exhibit such advantages to fall within the scope of the invention. Accordingly, the invention is not limited except as by the appended claims.

I claim:

1. A method for treating cardiac tissue, the cardiac tissue including a primum, a secundum adjacent to the primum, and a patent foramen ovale, the method comprising:
   shrinking the primum at a first location spaced apart from the patent foramen ovale; and
   at least partially sealing the patent foramen ovale by applying energy at a second location at least closer to the patent foramen ovale than the first location.

2. The method of claim 1 wherein at least partially sealing the patent foramen ovale includes at least partially sealing the patent foramen ovale without simultaneously shrinking the primum at the first location.

3. The method of claim 1 wherein at least partially sealing the patent foramen ovale includes at least partially sealing the patent foramen ovale after shrinking the primum.

4. The method of claim 1 wherein at least partially sealing the patent foramen ovale includes at least partially sealing the patent foramen ovale before shrinking the primum.

5. The method of claim 1 wherein shrinking the primum includes tightening the primum.

6. The method of claim 1 wherein shrinking the primum includes heating the primum.

7. The method of claim 1 wherein shrinking the primum includes drawing portions of the primum together and fastening the portions with a mechanical fastener.

8. The method of claim 7 wherein fastening the portions includes fastening the portions with an adhesive.

9. The method of claim 1 wherein shrinking the primum includes exposing the primum to a chemical agent.

10. The method of claim 1 wherein shrinking the primum includes directing ultrasonic energy to the primum.

11. The method of claim 1, further comprising applying a vacuum to a first section and a second section of the primum to fold at least one of the first and second sections against the other, and wherein shrinking the primum includes applying heat to the first and second sections to fuse the first and second sections while the first and second sections are in contact with each other.

12. The method of claim 1 wherein shrinking the primum includes:
   placing an inflatable member against the primum, the inflatable member having at least one electrode; and
   applying energy to the at least one electrode.

13. The method of claim 1 wherein shrinking the primum includes placing multiple bi-polar electrodes against the primum and directing current to the electrodes.

14. The method of claim 1 wherein shrinking the primum includes placing at least one of a side surface and an end surface of an elongated electrode in contact with the primum, and passing an electrical current through the electrode.

15. The method of claim 1 wherein shrinking the primum includes placing an electrode in contact with the primum and passing electrical current through the electrode, and wherein the method further comprises bending and straightening a catheter working portion that includes the electrode so as to scan the electrode over the primum and shrink the primum at multiple locations.

16. The method of claim 1, further comprising clamping first and second sections of the primum between a first member and a second member to fold the first and second sections against each other, and wherein shrinking the primum includes heating the first and second sections with the first and second members while the first and second sections are in contact with each other.

17. The method of claim 1 wherein at least partially sealing the patent foramen ovale includes:
   inserting a portion of a catheter into the patent foramen ovale;
   drawing the primum and secundum into contact with each other by drawing a vacuum in a region adjacent to the primum and secundum via the catheter while the catheter is positioned within the patent foramen ovale; and
   applying RF energy to the primum and the secundum from an electrode positioned at least partially within the patency.

18. The method of claim 17 wherein shrinking the primum includes shrinking the primum prior to drawing a vacuum in the region adjacent to the primum and the secundum.

19. The method of claim 17, further comprising:
   guiding the insertion motion of the catheter with a guide wire;
   removing the guide wire from the opening; and
   applying RF energy after removing the guide wire from the opening.

20. The method of claim 17, further comprising:
   guiding the insertion motion of the catheter with a guide wire; and
   applying RF energy while the guide wire remains in the opening.

21. The method of claim 17 wherein applying RF energy includes applying RF energy via at least one monopolar electrode.

22. The method of claim 17, further comprising at least inhibiting sticking between the inserted portion of the catheter and the cardiac tissue by directing liquid outwardly from the catheter proximate to an interface between the catheter and the cardiac tissue.

23. The method of claim 17, further comprising maintaining a distal end of the catheter at a fixed position relative to the patent foramen ovale by drawing the primum and secundum toward the catheter while applying RF energy.

24. The method of claim 17, further comprising controlling an insertion distance of the catheter by inserting the catheter only as far as a vacuum port that is spaced apart from a distal tip of the catheter, and detecting the insertion distance when the vacuum port becomes sealed by cardiovascular tissue.

25. A method for treating cardiac tissue, the cardiac tissue including a primum, a secundum adjacent to the primum, and a patent foramen ovale, the method comprising:
  releasably tightening the primum at a first location spaced apart from the patent foramen ovale by drawing portions of the primum together;
  while the primum is releasably tightened, at least partially sealing the patent foramen ovale by applying energy at a second location at least closer to the patent foramen ovale than the first location; and
  releasing tension on the primum after at least partially sealing the patent foramen ovale and allowing the portions of the primum to move apart from each other.

26. The method of claim 25 wherein releasably tightening the primum includes clamping first and second sections of the primum between a first member and a second member to fold the first and second sections against each other.

27. The method of claim 25 wherein releasably tightening the primum includes clamping first and second sections of the primum between at least two members to fold the first and second sections against each other.

28. The method of claim 25 wherein releasably tightening the primum includes applying a vacuum to a first section and a second section of the primum to fold at least one of the first and second sections against the other.

29. The method of claim 25 wherein releasably tightening the primum includes applying a force to the primum via an inflatable member.

30. The method of claim 25 wherein at least partially sealing the patent foramen ovale includes:
  inserting a portion of a catheter into the patent foramen ovale;
  drawing the primum and secundum into contact with each other by drawing a vacuum in a region adjacent to the primum and secundum via the catheter while the catheter is positioned within the patent foramen ovale; and
  applying RF energy to the primum and the secundum from an electrode positioned at least partially within the patency.

31. A method for treating cardiac tissue, the cardiac tissue including a primum, a secundum adjacent to the primum, and a foramen ovale having a patency in the form of a tunnel between the primum and the secundum, the method comprising:
  inserting a catheter into a patient's heart;
  heating the primum at a location spaced apart from the patent foramen ovale to shrink the primum;
  moving at least a portion of the catheter toward the tunnel, while drawing a vacuum through the catheter via vacuum channels positioned in peripheral portions of at least one electrode located at a distal end of the catheter;
  inserting the distal end of the catheter into the tunnel;
  drawing at least one of the primum and the secundum into contact with the other by applying a vacuum to the primum and secundum from a location between the primum and the secundum and within the tunnel;
  detecting at least one of a drop in evacuated fluid flow and an increase in the differential pressure drawn as at least one of the primum and the secundum is drawn into contact with the other;
  continuing to apply a vacuum through the catheter via the vacuum channels to secure the position of the at least one electrode relative to the primum and the secundum;
  applying radio frequency energy to the primum and the secundum via the at least one electrode to seal the tunnel; and
  supplying an electrolyte through a porous portion of the at least one electrode to at least restrict sticking between the at least one electrode and the tunnel.

32. The method of claim 31, further comprising applying a vacuum to the primum at the location spaced apart from the patent foramen ovale to draw sections of the primum against each other, and wherein heating the primum includes supplying RF energy to the primum to shrink the primum.

33. A method for treating cardiac tissue, the cardiac tissue including a primum and a secundum adjacent to the primum, the method comprising:
  drawing a first section and a second section of the primum together; and
  applying energy to the first and second sections of the primum to fuse the first and second sections to each other.

34. The method of claim 33 wherein drawing the first and second sections of the primum together includes applying a vacuum to first and second sections.

35. The method of claim 33 wherein the cardiac tissue further includes a patent foramen ovale, and wherein drawing the first and second sections of the primum together includes applying a vacuum at a first location spaced apart from the patent foramen ovale, and wherein the method further comprises at least partially sealing the patent foramen ovale by applying energy at a second location closer to the patent foramen ovale than the first location, after applying energy to the primum.

36. The method of claim 33 wherein applying a vacuum includes drawing the first and second sections of the primum into a vacuum opening.

37. The method of claim 33 wherein applying a vacuum includes drawing the first and second sections of the primum into contact with corresponding first and second electrodes.

38. The method of claim 33 wherein applying a vacuum includes drawing the first and second sections of the primum into contact with corresponding first and second semi-cylindrical electrodes.

39. The method of claim 33 wherein drawing the first and second sections of the primum together includes folding at least one of the first and second sections against the other.

40. The method of claim 33 wherein drawing the first and second sections of the primum together includes clamping the first section of the primum against the second section of the primum between at least a first member and a second member to fold the first and second sections against each other.

41. The method of claim 33 wherein the cardiac tissue further includes a patent foramen ovale, and wherein applying energy to the first and second sections of the primum includes applying energy at a first location of the primum spaced apart from the patent foramen ovale, and wherein the method further comprises at least partially sealing the patent foramen ovale by applying energy at a second location at least closer to the patent foramen ovale than the first location.

42. The method of claim 33 wherein the cardiac tissue further includes a patent foramen ovale, and wherein applying energy to the first and second sections of the primum includes applying energy at a first location of the primum spaced apart from the patent foramen ovale, and wherein the method further comprises at least partially sealing the patent foramen ovale by applying energy at a second location at least partially within the patent foramen ovale.

* * * * *

UNITED STATES PATENT AND TRADEMARK OFFICE
CERTIFICATE OF CORRECTION

| | | |
|---|---|---|
| PATENT NO. | : 7,473,252 B2 | |
| APPLICATION NO. | : 11/243324 | |
| DATED | : January 6, 2009 | |
| INVENTOR(S) | : David C. Auth et al. | |

It is certified that error appears in the above-identified patent and that said Letters Patent is hereby corrected as shown below:

In Title page, column 1, line 1, delete "Robert L. Barry, Kirkland, WA (US)" and insert -- David C. Auth, Kirkland WA (US); Joseph E. Eichinger, Everett, WA (US); Robert L. Barry, Kirkland, WA (US); Mark A. Tempel, Sammamish, WA (US); Christopher C. Genau, Seattle, WA (US); Ryan E. Kaveckis, Everett, WA (US); Blair J. Erbstoeszer, Kirkland, WA (US); James Anderson, Bothell, WA (US). --, therefor.

In page 4, column 1, line 11, delete "Foremen" and insert -- Foramen --, therefor.

In page 4, column 2, line 10, delete "foremen" and insert -- foramen --, therefor.

In page 4, column 2, line 30, delete "Thromboisis" and insert -- Thrombosis --, therefor.

In page 4, column 2, line 31, delete "May" and insert -- Mayo --, therefor.

In page 4, column 2, line 36, delete "Frequesently" and insert -- Frequently --, therefor.

In page 4, column 2, line 38, delete "Abnormabilites" and insert -- Abnormalities --, therefor.

In column 2, line 43, delete "FIG." and insert -- FIGS. --, therefor.

In column 3, line 10, delete "foraman" and insert -- foramen --, therefor.

In column 3, line 12, delete "foraman" and insert -- foramen --, therefor.

In column 3, line 13, delete "foraman" and insert -- foramen --, therefor.

In column 3, line 14–15, delete "foraman" and insert -- foramen --, therefor.

In column 3, line 16, delete "foraman" and insert -- foramen --, therefor.

UNITED STATES PATENT AND TRADEMARK OFFICE
CERTIFICATE OF CORRECTION

PATENT NO.         : 7,473,252 B2
APPLICATION NO.    : 11/243324
DATED              : January 6, 2009
INVENTOR(S)        : David C. Auth et al.

It is certified that error appears in the above-identified patent and that said Letters Patent is hereby corrected as shown below:

In column 3, line 19, delete "foraman" and insert -- foramen --, therefor.

Signed and Sealed this

Second Day of June, 2009

JOHN DOLL
*Acting Director of the United States Patent and Trademark Office*